(12) United States Patent
Casciola-Rosen et al.

(10) Patent No.: US 8,778,618 B2
(45) Date of Patent: Jul. 15, 2014

(54) COMPOSITIONS AND METHODS FOR CHARACTERIZING A MYOPATHY

(75) Inventors: Livia Angela Casciola-Rosen, Pikesville, MD (US); Lisa Christopher-Stine, Baltimore, MD (US); Andrew Mammen, Baltimore, MD (US); Antony Rosen, Pikesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/641,606

(22) PCT Filed: Apr. 15, 2011

(86) PCT No.: PCT/US2011/032710
§ 371 (c)(1),
(2), (4) Date: Oct. 16, 2012

(87) PCT Pub. No.: WO2011/130647
PCT Pub. Date: Oct. 20, 2011

(65) Prior Publication Data
US 2013/0040308 A1    Feb. 14, 2013

Related U.S. Application Data

(60) Provisional application No. 61/324,857, filed on Apr. 16, 2010, provisional application No. 61/371,798, filed on Aug. 9, 2010.

(51) Int. Cl.
*G01N 33/53* (2006.01)
(52) U.S. Cl.
USPC ............................................ 435/7.1; 435/7.2
(58) Field of Classification Search
None
See application file for complete search history.

(56) References Cited

U.S. PATENT DOCUMENTS 7,432,067 B2   10/2008   Nelson et al.
2004/0241169 A1   12/2004   Lowy et al.

FOREIGN PATENT DOCUMENTS

SE   WO 2009138130   * 11/2009
WO   WO 2007/061995   5/2007

OTHER PUBLICATIONS

Lisa Christopher-Stine, et. al.: "A novel autoantiboudy recognizing 200-kd and 100-kd proteins is associated with an immune-mediated necrotizing myopathy",Arthritis & Rheumatism, May 23, 2010.
Lisa Christopher-Stine, et. al.: Retrieved from the Internet: URL:http://onlinelibrary.wiley.com/doi/10.1002/art.27572/full, 2010.
Andrew L. Mammen et al, "Autoantibodies against 3-hydroxy-3-methyglutaryl-coenzymeA reductase in patients with statin-associated autoimmune myopathy", Arthritis & Rheumatism, Mar. 1, 2011.
Clark et al: "Production and characterization of monoclonal antibodies to rat liver microsomal 3-hydroxy-3-methylglutaryl-coenzyme A reductase." Proceedings of the National Academy of Sciences, Jun. 1, 1982.
Ira N. Targoff: "Autoantibodies and their significance in myositis", Current Theumatology Reports, Aug. 1, 2008.
G.J.D Hengstman et al: "Anti-aging recognition particle autoantibodies; marker of a necrotising myopathy", Annals of the Rheumatic Diseases, May 25, 2006.
Andrew L. Mammen et al., "Autoantibodies Against 3-Hydroxy-3-Methylglutaryl-Coenzye A Reductase in Patients With Statin-Associated Autoimmune Myopathy", Arthritis and Rheumatism, vol. 63, No. 3, pp. 713-721, Mar. 2011 (American College of Rheumatology).
Lisa Christopher-Stine et al., "A Novel Autoantibody Recognizing 200-id and 100-id Proteins Is Associated With an Immune-Mediated Necrotizing Myopathy", Arthritis and Rheumatism, vol. 62, Nov. 9, pp. 2757-2766, Sep. 1010 (American College of Rheumatology), 2010.

* cited by examiner

*Primary Examiner* — Jacob Cheu
(74) *Attorney, Agent, or Firm* — Edwards Wildman Palmer LLP; Peter F. Corless; Richard B. Emmons

(57) ABSTRACT

The invention provides compositions, methods, and kits diagnosing, monitoring, and otherwise characterizing a myopathy and for detecting the presence of autoantibodies in a biological sample.

20 Claims, 8 Drawing Sheets

COMPOSITIONS AND METHODS FOR CHARACTERIZING A MYOPATHY

STATEMENT OF RIGHTS TO INVENTIONS MADE UNDER FEDERALLY SPONSORED RESEARCH

This work was supported by the following grants from the National Institutes of Health, Grant Nos: AR44684, R37DE12354, K23-AR-053197, and K08-AR-054783. The government has certain rights in the invention.

CROSS-REFERENCE TO RELATED APPLICATIONS

This application is a 35 U.S.C. §371 U.S. national stage entry of International Application PCT/US2011/032710 (WO 2011/130647) having an International filing date of Apr. 15, 2011 which claims the benefit of the following U.S. Provisional Application Nos.: 61/324,857, filed Apr. 16, 2010 and 61/371,798, filed Aug. 9, 2010, the entire contents of each of which are incorporated herein by reference.

BACKGROUND OF THE INVENTION

Adults with proximal muscle weakness, elevated creatine kinase (CK) levels, features of myopathy on electromyography (EMG), and evidence of muscle edema on magnetic resonance imaging (MRI) have a broad differential diagnosis that includes autoimmune myopathies, toxic myopathies, paraneoplastic myopathies, and muscular dystrophies. Myopathy is a frequent adverse side-effect that occurs in subjects administered statins to lower their cholesterol. The muscle pain experienced by these patients is sometimes severe enough to warrant termination of statin therapy. Distinguishing between immune-mediated myopathies and other etiologies is crucial, because only autoimmune muscle diseases routinely respond to immunosuppressive therapy.

In many cases, distinctive clinical features and/or a muscle biopsy can provide a definitive diagnosis. For example, perifascicular atrophy is pathognomonic for dermatomyositis (DM) even in the absence of rash; vacuolar myopathy in a patient treated with colchicine strongly suggests a toxic myopathy, and reduced dystrophin staining in the muscle of a young man with calf hypertrophy is diagnostic for a dystrophinopathy.

However, in a substantial number of cases, muscle biopsy specimens show degenerating and necrotic muscle fibers in the absence of disease-specific features. In these instances, the presence of myositis-specific autoantibodies (MSAs) may identify the disorder as belonging to the family of autoimmune myopathies. For example, patients with antibodies directed against the signal recognition particle (SRP) typically have a severe necrotizing myopathy that is responsive only to very aggressive immunosuppression. Unfortunately, clinical evaluation and currently available diagnostic tests do not always provide a definitive diagnosis, and it may not be possible to determine whether a necrotizing myopathy is immune mediated. This uncertainty can lead to undertreatment of autoimmune myopathies or inappropriate immunosuppression in patients who do not have an immune-mediated disease. In sum, current clinical methods are inadequate to diagnose specific muscle diseases in patients experiencing myopathies and improved methods are urgently required.

SUMMARY OF THE INVENTION

As described below, the present invention features compositions, methods, and kits for treating, diagnosing, monitoring, and otherwise characterizing a myopathy (e.g., immune-mediated necrotizing myopathy) in a subject.

In one aspect, the invention provides a method for detecting an autoimmune response in a subject, the method comprising detecting in a biological sample of the subject an autoantibody that recognizes a 3-hydroxy-3-methylglutaryl coenzyme A reductase (HMGCR) protein.

In another aspect, the invention provides a method for characterizing a myopathy in a subject, the method comprising detecting in a biological sample of the subject an autoantibody that recognizes a 3-hydroxy-3-methylglutaryl coenzyme A reductase (HMGCR) protein.

In another aspect, the invention provides a method for characterizing a myopathy in a subject, the method comprising detecting in a biological sample of the subject a 100 kD protein and/or a 200 kD protein that binds an HMGCR antibody.

In another aspect, the invention provides a method for determining whether statin therapy should be continued in a subject, the method comprising assaying the presence of an autoantibody that recognizes a 3-hydroxy-3-methylglutaryl coenzyme A reductase (HMGCR) protein in a biological sample of the subject, wherein identification of the autoantibody indicates that statin therapy should be discontinued. In one embodiment, the absence of the autoantibody in a subject identified as having muscle pain indicates that statin therapy may be continued while the subject is monitored periodically for development of the autoantibody. In another embodiment, identification of the autoantibody in a subject having muscle pain and weakness indicates that statin therapy should be discontinued and that immunosuppressive therapy should be initiated.

In another aspect, the invention provides a method for monitoring statin therapy in a subject, the method comprising periodically testing a biological sample from the subject for an autoantibody that recognizes a 3-hydroxy-3-methylglutaryl coenzyme A reductase (HMGCR) protein in a biological sample of the subject. In one embodiment, the periodic testing is carried out at 3, 6, 9, 12, 24, and/or 36 months after initiation of statin therapy. In another embodiment, the method further comprises identifying the subject as having muscle pain or weakness subsequent to the initiation of statin therapy.

In another aspect, the invention provides a method of selecting a treatment regimen for a subject identified as having a myopathy, the method comprising detecting in a biological sample of the subject an autoantibody that recognizes a 3-hydroxy-3-methylglutaryl coenzyme A reductase (HMGCR) protein, wherein detection of the autoantibody indicates that immunosuppressive therapy should be selected. In one embodiment, the method further comprises identifying the subject as having muscle pain and weakness. In another embodiment, the biological sample is a liquid biological sample or a tissue sample. In another embodiment, the liquid biological sample is blood, serum, or plasma. In another embodiment, the autoantibody is detected in an immunoassay (e.g., an ELISA, immunoprecipitation, fluorescent immunosorbent assay, chemical linked immunosorbent assay, radioimmunoassay, immunoblotting, immunometric assay, flow cyotometry, western blot, or immunohistochemistry).

In another aspect, the invention provides a method for characterizing a myopathy in a subject, the method comprising contacting a 3-hydroxy-3-methylglutaryl coenzyme A reductase (HMGCR) protein or fragment thereof with serum, blood, or plasma of a subject, and detecting specific binding of an autoantibody to the HMGCR or fragment thereof, thereby characterizing a myopathy in a subject. In one embodiment, the HMGCR protein or fragment thereof is fixed to a substrate. In another embodiment, the substrate is a membrane, a bead, or a microchip. In another embodiment, binding is detecting using a colorimetric or radioactive assay.

In another aspect, the invention provides a kit for characterizing a myopathy in a subject, the kit comprising a 3-hydroxy-3-methylglutaryl coenzyme A reductase (HMGCR) protein or fragment thereof fixed to a substrate. In one embodiment, the kit further comprises instructions for the use of the kit in a method of any previous aspect. In one embodiment, the substrate is a membrane, a bead, or a microchip. In another embodiment, binding is detecting using a colorimetric assay. In another embodiment, the HMGCR fragment comprises a C-terminal fragment comprising aa 340-888.

In various embodiments of any of the above aspects or of any other aspect of the invention delineated herein, the method further involves detecting in a biological sample of the subject a 100 kD protein and/or a 200 kD protein that binds an HMGCR antibody. In certain embodiments of the above aspects, the protein is detected by immunoprecipitation. In other embodiments of the above aspects, HMGCR antibody binding to the 100 kD and/or 200 kD protein is detected in a colorimetric or radioactive assay. In still other embodiments, the myopathy is an autoimmune-mediated myopathy or necrotizing myopathy associated with statin therapy. In yet other embodiments, the method further involves characterizing proximal muscle strength, muscle edema on bilateral thigh MRI, creatine kinase levels, and/or myopathic findings on electromyography. In still other embodiments, the method involves detecting a marker selected from the group consisting of antisynthetase autoantibodies, anti-signal recognition particle (SRP) autoantibodies, elevated creatine kinase (CK) levels, marked inflammatory cell infiltrates in muscle biopsy, rimmed vacuoles, perifascicular atrophy, class I MHC positive, membrane attack complex deposition in small perimysial blood vessels, and anti-NCAM antibody staining of regenerating muscle fibers. In still other embodiments, the detecting involves comparing the level of autoantibodies in a subject sample to a reference level (e.g., the mean level present in a group of normal controls). In certain embodiments of the above aspects, detection of an about 2-5 standard deviation increase in level of the autoantibody that recognizes 3-hydroxy-3-methylglutaryl coenzyme A reductase (HMGCR) protein relative to a reference is indicative of statin-associated autoimmune myopathy. In other embodiments, detection of an about 3 standard deviation increase in level of the autoantibody is indicative of statin-associated autoimmune myopathy. In still other embodiments of the above aspects, the method further comprises identifying the subject as having muscle pain and weakness. In still other embodiments, the biological sample is a liquid biological sample or a tissue sample. In other embodiments, the liquid biological sample is blood, serum, or plasma. In other embodiments, the autoantibody is detected in an immunoassay (e.g., an ELISA, immunoprecipitation, fluorescent immunosorbent assay, chemical linked immunosorbent assay, radioimmunoassay, immunoblotting, immunometric assay, flow cyotometry, western blot, or immunohistochemistry). In certain embodiments of the above aspects, the HMGCR fragment comprises a C-terminal fragment comprising aa 340-888.

The invention provides methods for characterizing myopathy, particularly myopathies associated with statin therapy. Compositions and articles defined by the invention were isolated or otherwise manufactured in connection with the examples provided below. Other features and advantages of the invention will be apparent from the detailed description, and from the claims.

BRIEF DESCRIPTION OF THE FIGURES

FIGS. 3A-3D include photomicrographs showing membrane attack complex deposition on small blood vessels and non-necrotic myofibers. Serial section of a muscle biopsy specimen obtained from an anti-200/100 antibody-positive patient with necrotizing myopathy (patient 8076). Staining with anti-membrane attack complex (FIG. 3A) or hematoxylin and eosin (FIG. 3B) demonstrated a perimysial blood vessel with marked complement deposition. FIG. 3C is a muscle biopsy specimen obtained from an anti-200/100 antibody-positive patient (patient 8024) showing membrane attack complex deposition on scattered non-necrotic fibers. In FIG. 3D arrows indicate the absence of membrane attack complex staining of endomysial capillaries. Asterisks in FIGS. 3C and 3D show matching myofiber. (Original magnification ×40 in FIGS. 3A, 3B, and 3D; ×20 in FIG. 3C. Asterisks in FIGS. 3C and 3D mark the same myofiber.

FIG. 4A shows anti-class I MHC antibody staining of the endomysial capillaries of normal human muscle (arrow), but not the sarcolemma. FIGS. 4B and 4C show anti-class I MHC antibody staining of Class I major Anti-class I MHC antibody staining of the endomysial capillaries of normal human muscle (arrow), but not the sarcolemma. the sarcolemma of scattered muscle fibers in 2 patients with anti-200/100 autoantibodies (single asterisks). The cytoplasm of an anti-200/100 antibody-positive fiber also stained with anti-class I MHC (double asterisks); this likely represents a regenerating fiber. These biopsy specimens were processed simultaneously under identical conditions. (Original magnification ×40.)

In FIG. 5B, $^{35}$S-methionine-labeled full-length in vitro transcription/translated (IVTT) HMG-CoA reductase protein was immunoprecipitated using sera from anti-200/100-kd-positive patients (lanes 3-7; representative of 16 anti-200/100-kd-positive serum samples tested), anti-200/100-kd-negative patients with dermatomyositis (lanes 8-10), or healthy controls (lanes 11-13). The input IVTT product is shown in lane 14. Results in A and B are representative of at least 3 separate experiments. Molecular weight markers are shown at the left.

FIG. 3A shows the results of competition immunoprecipitation (IP) experiments, confirming that human anti-3-hydroxy-3-methylglutaryl-coenzyme A reductase (anti-HMGCR) antibodies detect the C-terminus and that the 200-kd protein is not recognized by a unique autoantibody. Serum samples 10009 and 9190 were preincubated with the indicated amounts of unlabeled C-terminal HMGCR and then used to immunoprecipitate full-length $^{35}$S-methionine-labeled HMGCR. In FIG. 3B, serum samples from patients 9190 and 9176 were preincubated in the absence or presence of 300 ng of unlabeled C-terminal HMGCR and were subsequently added to radiolabeled lysates generated from HeLa cells treated with 10 µM mevinolin for twenty-four hours. The resulting immunoprecipitates were processed as described herein below. Identical data were obtained in two separate experiments using four (7A) or six (7B) different patient sera. Molecular weight markers are shown at the left.

DEFINITIONS

Figure 1:
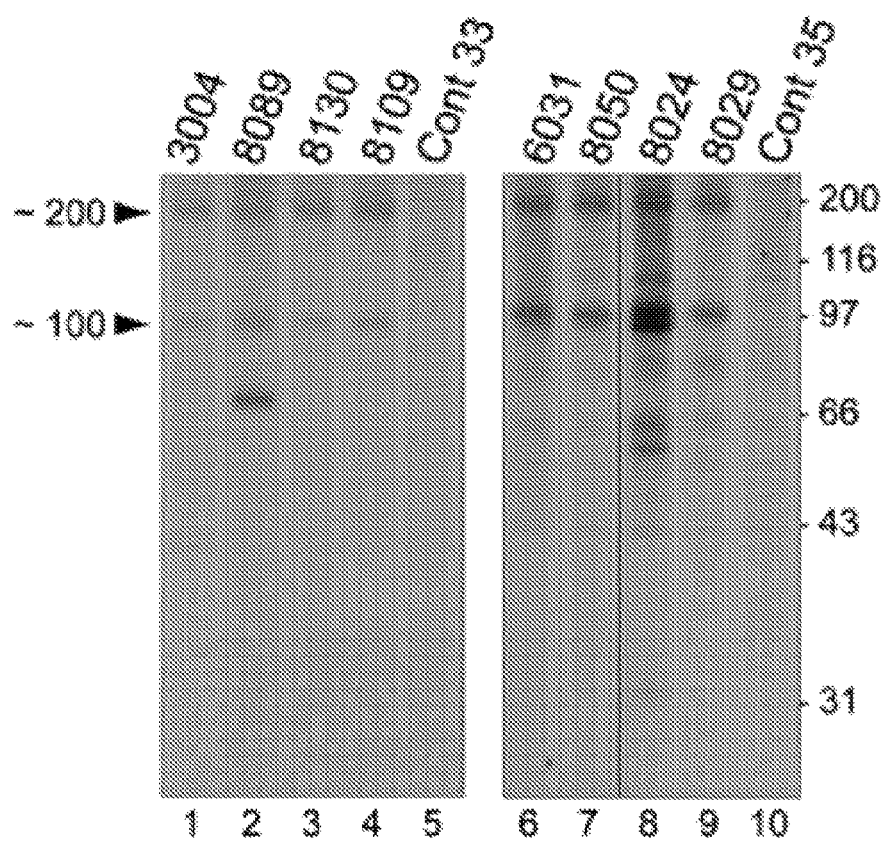
FIG. 1 includes an autoradiograph showing proteins immunoprecipitated from HeLa cell extracts by sera from patients having a necrotizing myopathy. Immunoprecipitation of ~200-kd and ~100-kd proteins by sera from patients with a necrotizing myopathy. Patient sera were used to immunoprecipitate radioactively labeled proteins from HeLa cell extracts that had been incubated with $^{35}$S-methionine. Immunoprecipitated proteins were separated by electrophoresis on 10% sodium dodecyl sulfate-polyacrylamide gels. The left and right panels show autoradiographs from two separate experiments; results shown in the right panel are from a single autoradiograph that has been cropped between lanes 7 and 8 to exclude immunoprecipitations that are irrelevant to the current study. The numbers at the top of lanes 1-4 and 6-9 are patient numbers. Sera from two normal control sera (Cont 33 and Cont 35) were used for the immunoprecipitations shown in lanes 5 and 10. Arrowheads on the left side point out the ~200-kD and ~100-kD protein bands. Values on the far right indicate positions of molecular weight marker standards.

By "3-hydroxy-3-methylglutaryl coenzyme A reductase (HMGCR) protein" is meant a polypeptide or fragment thereof having at least about 85% amino acid sequence identity to NCBI Ref: NP_000850.1 or a fragment thereof having HMGCR antibody binding activity. One preferred fragment is a C-terminal fragment including the intracellular portion of the molecule (aa 340-888), which is shown in bold/underline below.

An exemplary HMGCR protein sequence is provided below:

```
>gi|4557643|ref|NP_000850.1| 3-hydroxy-3-methylglutaryl-Coenzyme
A reductase isoform 1 [Homo sapiens]
MLSRLFRMHGLFVASHPWEVIVGTVTLTICMMSMNMFTGNNKICGWNYECPKFEEDVLSSDIIILTITRC

IAILYIYFQFQNLRQLGSKYILGIAGLFTIFSSFVFSTVVIHFLDKELTGLNEALPFFLLLIDLSRASTL

AKFALSSNSQDEVRENIARGMAILGPTFTLDALVECLVIGVGTMSGVRQLEIMCCFGCMSVLANYFVFMT

FFPACVSLVLELSRESREGRPIWQLSHFARVLEEEENKPNPVTQRVKMIMSLGLVLVHAHSRWIADPSPQ

NSTADTSKVSLGLDENVSKRIEPSVSLWQFYLSKMISMDIEQVITLSLALLLAVKYIFFEQTETESTLSL

KNPITSPVVTQKKVPDNCCRREPMLVRNNQKCDSVEEETGINRERKVEVIKPLVAETDTPNRATFVVGNS

SLLDTSSVLVTQEPEIELPREPRPNEECLQILGNAEKGAKFLSDAEIIQLVNAKHIPAYKLETLMETHER

GVSIRRQLLSKKLSEPSSLQYLPYRDYNYSLVMGACCENVIGYMPIPVGVAGPLCLDEKEFQVPMATTEG

CLVASTNRGCRAIGLGGGASSRVLADGMTRGPVVRLPRACDSAEVKAWLETSEGFAVIKEAFDSTSRFAR

LQKLHTSIAGRNLYIRFQSRSGDAMGMNMISKGTEKALSKLHEYFPEMQILAVSGNYCTDKKPAAINWIE

GRGKSVVCEAVIPAKVVREVLKTTTEAMIEVNINKNLVGSAMAGSIGGYNAHAANIVTAIYIACGQDAAQ

NVGSSNCITLMEASGPTNEDLYISCTMPSIEIGTVGGGTNLLPQQACLQMLGVQGACKDNPGENARQLAR

IVCGTVMAGELSLMAALAAGHLVKSHMIHNRSKINLQDLQGACTKKTA
```

By "autoantibody" is meant an antibody that is directed against an autoantigen. An exemplary autoantibody is one that is directed against HMGCR.

By "HMGCR antibody" is meant an antibody that specifically binds HMGCR protein.

By "myopathy" is meant a muscular condition associated with muscular weakness or pain. Other markers of myopathy include, but are not limited to the presence of antisynthetase autoantibodies, anti-signal recognition particle (SRP) autoantibodies, elevated creatine kinase (CK) levels, marked inflammatory cell infiltrates in muscle biopsy, rimmed vacuoles, perifascicular atrophy, class I MHC positive, membrane attack complex deposition in small perimysial blood vessels, and anti-NCAM antibody staining of regenerating muscle fibers. Other markers include proximal muscle weakness, evidence of myopathy on electromyography (EMG), marked inflammatory cell infiltrates in muscle biopsy, rimmed vacuoles, perifascicular atrophy, and muscle edema on bilateral thigh MRI.

By "immunoassays" is meant a test that measures the presence or level of a substance based on specific antibody binding.

By "immunosuppression" is meant reducing at least one undesirable function of the immune system.

By "immunosuppressant" is meant an agent that reduces immune system function. Examples of immunosuppressants include glucocorticoids (e.g., prednisone), cytostatics (e.g., azathioprine and methotrexate), drugs acting on immunophilins (e.g., cyclosporine and tacrolimus), and other drugs (e.g., hydroxychloroquine, intravenous immunoglobulin, mycophenylate mofetil, and rituximab).

By "substrate" is meant any solid support. Exemplary solid supports include a microtiter plate, a microscope slide, a polystyrene bead, a test tube, a lateral flow device, a test strip, or a dipstick.

By "statin" is meant a class of drug used to lower cholesterol levels by inhibiting the enzyme HMG-CoA reductase. Examples of statins include atorvastatin (Lipitor® and Torvast), fluvastatin (Lescol), lovastatin (Mevacor®, Altocor, Mevinolin, and Altoprev®), pitavastatin (Livalo®, Pitava), pravastatin (Pravachol, Selektine, and Lipostat), rosuvastatin (Crestor®) and simvastatin (Zocor® and Lipex™).

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard n known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "biologic sample" is meant any tissue, cell, fluid, or other material derived from an organism.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "control" is meant a standard of comparison. For example, the level of an autoantibody in a sample from a subject suspected of having an immune mediated necrotizing myopathy may be compared to the level of the autoantibody present in a corresponding sample from a normal subject, i.e., one who does not have a myopathy.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "diagnostic" is meant any method that identifies the presence of a pathologic condition or characterizes the nature of a pathologic condition (e.g., a myopathy). Diagnostic methods differ in their sensitivity and specificity. While a particular diagnostic method may not provide a definitive diagnosis of a condition, it suffices if the method provides a positive indication that aids in diagnosis.

By "disease" is meant any condition or disorder that damages or interferes with the normal function of a cell, tissue, or organ. Examples of diseases include autoimmune disease, myopathy, and autoimmune statin-associated myopathy.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any alteration in a protein, polynucleotide, or clinical indicator that is associated with a disease or disorder.

As used herein, "obtaining" as in "obtaining an agent" includes synthesizing, purchasing, or otherwise acquiring the agent.

By "periodic" is meant at regular intervals. Periodic patient monitoring includes, for example, a schedule of tests occur, weekly, monthly, bi-annually, or annually.

By "reduces" or "increases" is meant a negative or positive alteration, respectively, of at least about 10%, 25%, 50%, 75%, or 100% relative to a reference.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention features compositions and methods that are useful for compositions, methods, and kits for treating, diagnosing, monitoring, and otherwise characterizing a myopathy (e.g., immune-mediated necrotizing myopathy) in a subject.

The invention is based, at least in part, on the discovery that in certain patients statin-use is associated with an autoimmune-mediated necrotizing myopathy with autoantibodies that recognize 3-hydroxy-3-methylglutaryl coenzyme A reductase (HMGCR) protein.

As reported in detail below, the discovery of novel autoantibodies in patients with necrotizing myopathy was made when characterizing patients having myofiber necrosis without prominent inflammation, a nonspecific finding in patients with dystrophies and toxic or immune-mediated myopathies. Since the etiology of a necrotizing myopathy is often obscure, the question of how to treat these patients, i.e., whether they would benefit from immunosuppression, remained unanswered. To develop a method for diagnosing and treating such necrotizing myopathy patient, muscle biopsy specimens and serum samples from 225 patients with myopathy were analyzed. Antibody specificities were determined by performing immunoprecipitations from $^{35}$S-methionine-labeled HeLa cell lysates. Selected biopsy specimens were stained for membrane attack complex, class I major histocompatibility complex (MHC), and endothelial cell marker CD31. Muscle biopsy specimens from thirty-eight of the 225 patients showed predominantly myofiber necrosis. Twelve of these patients had a known autoantibody association with or other etiology for their myopathy. Sixteen of the remaining twenty-six sera immunoprecipitated 200-kD and 100-kD proteins; this specificity was observed in only one of 187 patients without necrotizing myopathy. Patients with the anti-200/100-kD autoantibody 10,333 IU/liter), and an irritable myopathy on electromyography (88%). Sixty-three percent of these patients had been exposed to statins prior to the onset of weakness. All patients responded to immunosuppressive therapy, and many experienced a relapse of weakness when the medication was tapered. Immunohistochemical studies showed membrane attack complex on small blood vessels in six of eight patients and on the surface of non-necrotic myofibers in four of eight patients. Five of eight patients had abnormal capillary morphology, and four of eight patients expressed class I MHC on the surface of non-necrotic myofibers. From these data, it is clear that an anti-200/100-kD autoantibody specificity defines a subgroup of patients with necrotizing myopathy who previously were considered to be autoantibody negative. Following the initial discovery of novel autoantibodies in patients with necrotizing myopathy, additional experiments were undertaken, as reported in detail below, to identify the 200-kD and 100-kD autoantigens targeted by the autoantibodies in an effort to help clarify the disease mechanism of immune-mediated necrotizing myopathy (IMNNI) and facilitate its diagnosis. In addition to inducing a self-limited myopathy, statin use is associated with an immune-mediated necrotizing myopathy (IMNM), with auto-antibodies that recognize 200-kd and 100-kd autoantigens. To identify these molecules, the effects of statin treatment on auto-antigen expression was addressed by immunoprecipitation using sera from patients. The identity of the ~100-kD autoantigen was confirmed by immunoprecipitation of in vitro-transcribed/translated (IVTT) 3-hydroxy-3-methylglutarylcoenzyme A reductase (HMG CoA reductase or HMGCR) protein. HMG CoA reductase expression in muscle was analyzed by immunofluorescence. A cohort of myopathy patients was screened for anti-HMG CoA reductase autoantibodies by enzyme-linked immunosorbent assay (ELISA) and genotyped for the rs4149056 C allele, a predictor of self-limited statin myopathy. Statin exposure induced expression of the ~200-kD/~100-kD autoantigens in cultured cells. HMG CoA reductase was identified as the 100-kD autoantigen. Competition experiments demonstrated no distinct auto-antibodies recognizing the ~200-kD protein. In muscle biopsy tissues from anti-HMG CoA reductase autoantibody-positive patients, HMG CoA reductase expression was up-regulated in cells expressing neural cell adhesion molecule (NCAM), a marker of muscle regeneration. Anti-HMG CoA reductase autoantibodies were found in forty-five of 750 patients presenting to the Johns Hopkins Myositis Center (6%). Among patients ages fifty years and older, 92.3% had taken statins. The prevalence of the rs4149056 C allele was not increased in patients with anti-HMG CoA reductase autoantibody positivity. Statins up-regulated the expression of HMGCR, the major target of autoantibodies in statin-associated IMNM. Regenerating muscle cells express high levels of HMGCR, which may sustain the immune response even after statins are discontinued. These studies demonstrate a mechanistic link between an environmental trigger and the development of sustained autoimmunity.

These findings indicate that statin use triggers an autoimmune response against HMG CoA reductase by up-regulating the expression of this autoantigen. Even after discontinuing statin use, the presence of high levels of HMG CoA reductase in regenerating muscle fibers perpetuates the immune response, subjects taking statins should be monitored for the presence of autoantibodies. If autoantibodies are detected in a subject taking a statin he/she should discontinue taking the statin and should be treated with immunosuppressive therapy to prevent or reduce the severity of immune-mediated myopathic symptoms. As evident from the below Examples and elsewhere in this application, detection of anti-HMG CoA reductase autoantibodies facilitates diagnosis and direct therapy of an immune-mediated necrotizing myopathy.

Statins:

Statins lower cholesterol levels by specifically inhibiting 3-hydroxy-3-methylglutaryl-coenzyme A reductase (HMG CoA reductase or HMGCR), a key enzyme in the cholesterol biosynthesis pathway. These drugs significantly reduce cardiovascular end points and are among the most commonly prescribed medications, with almost 30 million people in the US prescribed a statin in 2005 (Stagnitti M N. Rockdale (MD): Agency for Healthcare Research and Quality; 2008 May. Statistical brief 205). Examples of statins include atorvastatin (Lipitor® and Torvast), fluvastatin (Lescol), lovastatin (Mevacor®, Altocor, Mevinolin, and Altoprev®), pitavastatin (Livalo®, Pitava), pravastatin (Pravachol, Selektine, and Lipostat), rosuvastatin (Crestor®) and simvastatin (Zocor® and Lipex™).

Musculoskeletal symptoms are a well-known complication of statin use and range from myalgias and cramps, which occur in 9-20% of statin users (De Sauvage Nolting et al., *Am J Cardiol* 2002; 90:181-4; Bruckert et al., *Cardiovasc Drugs Ther* 2005; 19:403-14; and Franc et al., *Cardiovasc Drugs Ther* 2003; 17:459-65.), to life-threatening rhabdomyolysis, a rare event occurring at a rate of ~0.4 per 10,000 patient years (Graham et al., *JAMA* 2004; 292: 2585-90.).

In most cases, statin-induced myopathic events are self-limited, with complete recovery in the weeks or months after the statin is discontinued (Soininen et al., *Basic Clin Pharmacol Toxicol* 2006; 98:51-4). However, two recent studies have described thirty-three patients who developed an autoimmune myopathy following statin exposure, which did not abate after discontinuing the statins (Needham et al., *Neuromuscul Disord* 2007; 17: 194-200 and Grable-Esposito et al., *Muscle Nerve* 2010; 41:185-90.).

Diagnostics

The present invention features diagnostic assays for the detection of autoantibodies that recognize 3-hydroxy-3-methylglutaryl coenzyme A reductase (HMGCR) protein in a biological sample of a subject. In one embodiment, levels of such autoantibodies are measured in a subject sample and used to characterize autoimmune disease, myopathy associated with an autoimmune response associated with statin therapy, and necrotizing myopathy, or a propensity to develop such a condition. Standard methods may be used to measure levels of an autoantibody in a biological sample. Biological samples include tissue samples (e.g., cell samples, biopsy samples) and bodily fluids, including, but not limited to, blood, blood serum, and plasma. Methods for measuring levels of polypeptide include immunoassay, ELISA, western blotting and radioimmunoas say or any other method known in the art. Elevated levels of autoantibodies alone or in combination with one or more additional markers are considered a positive indicator of autoimmune disease. The increase in autoantibodies may be by at least about 10%, 25%, 50%, 75% or more. In one embodiment, any increase in a marker of the invention is indicative of autoimmune disease, myopathy, or necrotizing myopathy.

Any suitable method can be used to detect autoantibodies and other markers described herein that are useful in defining the etiology of a myopathy. In particular, autoantibodies that recognize 3-hydroxy-3-methylglutaryl coenzyme A reductase (HMGCR) protein can be used alone or in combination with antisynthetase autoantibodies (anti-Jo-1, anti-PL-12, anti-PL-7), anti-signal recognition particle (SRP) autoantibodies. Other clinical indicators of myopathy may also be evaluated, including but not limited to, proximal muscle weakness, elevated creatine kinase (CK) levels, evidence of myopathy on electromyography (EMG), marked inflammatory cell infiltrates in muscle biopsy, perifascicular atrophy, muscle edema on bilateral thigh MRI, class I MHC positive, membrane attack complex deposition in small perimysial blood vessels, and anti-NCAM antibody staining to identify regenerating muscle tissues.

Successful practice of the invention can be achieved with one or a combination of methods that can detect and, preferably, quantify such markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero.

Detection methods may include use of a biochip array. Biochip arrays useful in the invention include protein and polynucleotide arrays. One or more markers are captured on the biochip array and subjected to analysis to detect the level of the markers in a sample.

Autoantibodies may be captured with capture reagents, such as a 3-hydroxy-3-methylglutaryl coenzyme A reductase (HMGCR) proteins or fragments thereof immobilized to a solid support, such as a biochip, a multiwell microtiter plate, a resin, or a nitrocellulose membrane that is subsequently probed for the presence or level of a marker. In one embodiment, the fragment is a C-terminal fragment including the intracellular portion of the molecule (aa 340-888). Capture can be on a chromatographic surface or a biospecific surface. For example, a sample containing the autoantibodies, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, autoantibodies can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

In one embodiment, the level of autoantibodies is measured on at least two different occasions and an alteration in the levels as compared to normal reference levels over time is used as an indicator of the presence or progression of autoimmune disease, myopathy, necrotizing myopathy. The level of marker in the bodily fluids (e.g., blood, blood serum, plasma) of a subject having autoimmune disease, myopathy, or necrotizing myopathy may be altered by as little as 10%, 20%, 30%, or 40%, or by as much as 50%, 60%, 70%, 80%, or 90% or more relative to the level of such marker in a normal control. In general, levels of autoantibodies that recognize 3-hydroxy-3-methylglutaryl coenzyme A reductase (HMGCR) protein are present at low or undetectable levels in a healthy subject (i.e., those who do not have and/or who will not develop myopathy). In one embodiment, a subject sample of a bodily fluid (e.g., blood, blood serum, plasma,) is collected prior to the onset of symptoms of myopathy, but subsequent to the initiation of statin therapy.

The diagnostic methods described herein can be used individually or in combination with any other diagnostic method described herein for a more accurate diagnosis of the presence or severity of myopathy.

The diagnostic methods described herein can also be used to monitor and manage myopathy, or to reliably distinguish a necrotizing myopathy from other myopathies.

As indicated above, the invention provides methods for aiding a human myopathy diagnosis using one or more markers, as specified herein. An autoantibody that recognize 3-hydroxy-3-methylglutaryl coenzyme A reductase (HMGCR) protein can be used alone, in combination with other autoantibodies associated with autoimmune myopathy, or with other clinical indicators useful in aiding human myopathy diagnosis. The autoantibodies are differentially present in samples of a human necrotizing myopathy patient and a normal subject in whom myopathy is undetectable. Therefore, detection of autoantibodies in a person would provide useful information regarding the probability that the person may have necrotizing myopathy or regarding their propensity to develop the disease.

The detection of autoantibodies that recognize 3-hydroxy-3-methylglutaryl coenzyme A reductase (HMGCR) protein is correlated with autoimmune disease, myopathy associated with an autoimmune response associated with statin therapy, and necrotizing myopathy. In some embodiments, the detection of the mere presence of autoantibodies that recognize 3-hydroxy-3-methylglutaryl coenzyme A reductase (HMGCR) protein, without quantifying the amount thereof, is useful and can be correlated with a probable diagnosis of myopathy. The measurement of autoantibodies may also involve quantifying the autoantibodies to correlate the detection of markers with a probable diagnosis of autoimmune disease, myopathy associated with an autoimmune response associated with statin therapy, and necrotizing myopathy.

Thus, if the amount of the markers detected in a subject being tested is different compared to a control amount (i.e., higher than the control), then the subject being tested has a higher probability of having autoimmune disease, myopathy associated with an autoimmune response associated with statin therapy, and necrotizing myopathy.

The correlation may take into account the amount of the autoantibodies in the sample compared to a control amount of the marker or markers (e.g., in normal subjects where myopathy is undetectable). A control can be, e.g., the average or median amount of autoantibodies present in comparable samples of normal subjects. The control amount is measured under the same or substantially similar experimental conditions as in measuring the test amount. As a result, the control can be employed as a reference standard, where the normal (non-myopathy) phenotype is known, and each result can be compared to that standard, rather than re-running a control.

In certain embodiments of the methods of diagnosing autoimmune disease, myopathy associated with an autoimmune response associated with statin therapy, and necrotizing myopathy, the methods further comprise managing subject treatment based on the status. The invention also provides for such methods where the markers (or specific combination of markers) are measured again after subject management. In these cases, the methods are used to monitor the status of the myopathy, e.g., response to myopathy treatment, remission of the disease or progression of the disease.

The diagnostics of the present invention, which include immunoassays used to detect the presence of or measure the level of autoantibodies in a biological sample of a subject have a number of other uses. For example, they can be used to monitor responses to certain treatments of autoimmune disease, myopathy associated with an autoimmune response associated with statin therapy, and necrotizing myopathy. In yet another example, the markers can be used in heredity studies. For instance, certain markers may be genetically linked. Markers that are genetically linked may be used as a tool to determine if a subject is genetically pre-disposed to having an autoimmune associated myopathy. For example, the presence of a specific polymorphism in the SLCO1B1 gene (i.e., the rs4149056 C allele) is strongly associated with the development of statin myopathy.

Any marker, individually, is useful in aiding in the determination of autoimmune disease, myopathy associated with an autoimmune response associated with statin therapy, and necrotizing myopathy. First, the autoantibodies that recognize 3-hydroxy-3-methylglutaryl coenzyme A reductase (HMGCR) protein is detected in a subject sample using the methods described herein. Then, the result is compared with a control that distinguishes an autoimmune based myopathy status from a control. As is well understood in the art, the techniques can be adjusted to increase sensitivity or specificity of the diagnostic assay depending on the preference of the diagnostician.

While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, preferred methods of the present invention comprise the measurement of more than one marker.

Diagnostic Assays

The present invention provides a number of diagnostic assays that are useful for the identification or characterization of autoimmune disease, myopathy associated with an autoimmune response associated with statin therapy, and necrotizing myopathy, or a propensity to develop such a condition. In one embodiment, myopathy is characterized by detecting the presence of autoantibodies that recognize 3-hydroxy-3-methylglutaryl coenzyme A reductase (HMGCR) protein, alone or in combination with one or more other markers used to characterize myopathy (e.g., antisynthetase autoantibodies, anti-signal recognition particle (SRP) autoantibodies, elevated creatine kinase (CK) levels, marked inflammatory cell infiltrates in muscle biopsy, perifascicular atrophy, class I MHC positive, membrane attack complex deposition in small perimysial blood vessels, and anti-NCAM antibody staining of regenerating muscle fibers). While the examples provided below describe specific methods of detecting levels of these markers, the skilled artisan appreciates that the invention is not limited to such methods. Autoantibody levels are quantifiable by any standard method, such methods include, but are not limited to immunoassays that detect antibody binding (e.g., ELISA, Western blot, immunoprecipitation, immunofluorescence). Such assays can be carried out on membranes, test strips, biochips, or any other platform known in the art.

Diagnostic Kits

The invention provides kits for diagnosing or monitoring an autoimmune disease, myopathy associated with an autoimmune response associated with statin therapy, and necrotizing myopathy, or for selecting a treatment for those conditions or any other condition associated with the presence of autoantibodies that recognize 3-hydroxy-3-methylglutaryl coenzyme A reductase (HMGCR) protein. In one embodiment, the kit is used to determine whether a subject should continue on statin therapy. In reaching this determination, the clinician may consider whether the subject has autoantibodies that recognize 3-hydroxy-3-methylglutaryl coenzyme A reductase (HMGCR) protein. Such antibodies can develop weeks, months, or even years after statin therapy is initiated. If desired, a subject on statin therapy is tested for such autoantibodies regardless of whether or not they are displaying symptoms of myopathy.

In one embodiment, the kit includes a composition containing at least one agent that binds an autoantibody that specifically binds 3-hydroxy-3-methylglutaryl coenzyme A reductase (HMGCR) protein. In certain embodiments, the agent that binds the autoantibody is a fragment of the HMGCR protein, for example, a C-terminal fragment. In some embodiments, the kit comprises a sterile container which contains the binding agent; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the kit is provided together with instructions for using the kit to diagnose autoimmune disease, myopathy associated with an autoimmune response associated with statin therapy, and/or necrotizing myopathy. The instructions will generally include information about the use of the composition for diagnosing a subject as having myopathy or having necrotizing myopathy. In other embodiments, the instructions include at least one of the following: description of the binding agent; warnings; indications; counter-indications; animal study data; clinical study data; and/or references. The instructions may be printed directly on the container (when present), or as a label applied to the container, or as a separate sheet, pamphlet, card, or folder supplied in or with the container.

Types of Biological Samples

The level of autoantibodies that recognize a 3-hydroxy-3-methylglutaryl coenzyme A reductase (HMGCR) protein is measured in different types of biologic samples. In one embodiment, the level of an autoantibody is measured in different types of biologic samples. In another embodiment, the level of autoantibody is measured in different types of biologic samples. In one embodiment, the biologic sample is a tissue sample that includes muscle cells (e.g., muscle cells obtained in a muscle biopsy). In another embodiment, the biologic sample is a biologic fluid sample. Biological fluid samples include blood, blood serum, plasma, saliva, or any other biological fluid useful in the methods of the invention.

Selection of a Treatment Method and Subject Monitoring

After a subject is identified as having an autoimmune disease, myopathy associated with an autoimmune response associated with statin therapy, and necrotizing myopathy, a method of treatment is selected. A number of standard treatment regimens are available. The level or presence of autoantibodies that recognize 3-hydroxy-3-methylglutaryl coenzyme A reductase (HMGCR) protein is one factor used in selecting a treatment method. In one embodiment, the presence of autoantibodies that recognize 3-hydroxy-3-methylglutaryl coenzyme A reductase (HMGCR) protein is indicative that immunosuppressive therapy is appropriate. Other relevant factors that may be used in conjunction with the presence of such autoantibodies are other markers and clinical indicators useful in defining a myopathy (e.g., antisynthetase autoantibodies, anti-signal recognition particle (SRP) autoantibodies, elevated creatine kinase (CK) levels, marked inflammatory cell infiltrates in muscle biopsy, rimmed vacuoles, perifascicular atrophy, class I MHC positive, membrane attack complex deposition in small perimysial blood vessels, and anti-NCAM antibody staining of regenerating muscle fibers).

The disease state or treatment of a subject having an autoimmune disease, myopathy associated with an autoimmune response associated with statin therapy, and necrotizing myopathy, or a propensity to develop such a condition can be monitored using the methods and compositions of the invention. In one embodiment, the expression of markers present in a bodily fluid, such as blood, blood serum, and plasma, is monitored. Such monitoring may be useful, for example, in assessing the efficacy of a particular drug (e.g., an immunosuppressive drug) in a subject exhibiting symptoms of myopathy. Desirably, treatment with the immunosuppressive drug reduces levels of autoantibodies that recognize 3-hydroxy-3-methylglutaryl coenzyme A reductase (HMGCR) protein. If such treatment does not reduce autoantibody levels, a different immunosuppressive therapy is indicated. For example, if autoantibody levels are not reduced in response to prednisone, combination immunosuppressive therapy is indicated. Such therapy may involve any two or more of the following prednisone, rituximab, intravenous immunoglobulin, azathioprine and/or methotrexate, or other immunomudulatory agents. Therapeutics that decrease the expression of a marker of the invention (e.g., autoantibodies that recognize 3-hydroxy-3-methylglutaryl coenzyme A reductase (HMGCR) protein) are taken as particularly useful in the invention.

Kits

The invention provides kits for the diagnosis of an autoimmune disease, myopathy associated with an autoimmune response associated with statin therapy, and necrotizing myopathy, particularly an autoimmune response associated with the presence of autoantibodies that recognize 3-hydroxy-3-methylglutaryl coenzyme A reductase (HMGCR) protein. In one embodiment, the kit includes an agent that binds autoantibodies that specifically bind 3-hydroxy-3-methylglutaryl coenzyme A reductase (HMGCR) protein. In one embodiment, this agent is fixed to a substrate.

The substrate is a solid support that may be in the shape of a paper strip, dipstick, membrane (e.g. a nylon membrane or a cellulose filter), a plate (e.g. a microtiter plate, 96-well plate) or solid particles (e.g. latex or magnetic beads). The solid support may be made of any suitable material, including but not limited to a plastic (e.g., polyethylene, polypropylene, polystyrene, latex, polyvinylchloride, polyurethane, polyacrylamide, polyvinylalcohol, nylon, polyvinyl acetate, or any suitable copolymers thereof), cellulose (e.g. various types of paper, such as nitrocellulose paper and the like), a silicon polymer (e.g. siloxane), a polysaccharide (e.g. agarose or dextran), or an ion exchange resin (e.g. conventional anion or cation exchange resins).

In other embodiments, the kit comprises the agent fixed to a substrate and other reagents useful in an ELISA. In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the kit includes instructions for using the kit to detect autoantibody binding to 3-hydroxy-3-methylglutaryl coenzyme A reductase (HMGCR) protein or a fragment thereof. The instructions will generally include information about the use of the composition for the diagnosis of an autoimmune disease, myopathy associated with an autoimmune response associated with statin therapy, and necrotizing myopathy. In other embodiments, the instructions include at least one of the following: description of the HMGCR binding agent; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

A Novel Anti-200/100-kD Autoantibody is Present Sera of Patients with a Necrotizing Myopathy Muscle biopsy specimens obtained from 225 patients who presented with proximal muscle weakness, elevated creatine kinase (CK) levels, evidence of myopathy on electromyography (EMG), and/or other evidence of muscle disease were reviewed in order to identify those with a predominantly necrotizing myopathy. Patients with biopsy results notable for marked inflammatory cell infiltrates, rimmed vacuoles (characteristic of inclusion body myositis), perifascicular atrophy (pathognomonic for dermatomyositis (DM), or other features characteristic of a specific diagnosis were not considered to have a predominantly necrotizing myopathy.

In all, thirty-eight patients (17% of the total) were identified as having a predominantly necrotizing myopathy on muscle biopsy. Of these, a specific muscle disease was definitively diagnosed in twelve patients, using existing testing methods. Ten patients had autoimmune myopathies as defined by the presence of antisynthetase autoantibodies (one with anti-Jo-1, two with anti-PL-12, and one with anti-PL-7) or by the presence of anti-signal recognition particle (SRP) autoantibodies (six patients); each of these patients also had a definite positive response to immunosuppressive therapy. In addition, one patient had a necrotizing myopathy associated with profound hypothyroidism and another had limb-girdle muscular dystrophy type 2B (i.e., dysferlinopathy), which was later confirmed by genetic testing. The remaining twenty-six patients (~10% of the original cohort) had a predominantly necrotizing myopathy of unclear etiology.

Sera collected from the twenty-six patients described above were screened for the presence of novel autoantibodies. Remarkably, sera from sixteen of these patients (62%) was found to have immunoprecipitated a pair of proteins from radioactively labeled HeLa cell extracts with approximate sizes of 200 kd and 100 kd, respectively (FIG. 1). These proteins, with molecular weights that do not correspond to those of known myositis-specific autoantigens, were always immunoprecipitated as a pair. Although anti-200/100-kD autoantibody immunoprecipitations were reproducible, no serum detected 200-kD or 100-kD proteins when used to immunoblot HeLa cell extracts.

In order to evaluate the specificity of these antibodies for a necrotizing phenotype, anti-200/100 autoantibody immunoreactivity was tested for in the remaining cohort. Among the 187 patients who did not have a predominant necrotizing myopathy, the serum from only 1 patient (0.5%) immunoprecipitated the 200-kd and 100-kd proteins, demonstrating that this finding is highly specific for those patients with a necrotizing myopathy ($P<10^{-15}$ by Fisher's exact test). None of the sera from the 12 patients with necrotizing myopathies associated with previously known conditions, including the 6 patients with anti-SRP antibodies, immunoprecipitated proteins with molecular weights of 200 kd or 100 kd.

Several of the anti-200/100-kD autoantibody-positive sera immunoprecipitated additional proteins. For example, the serum from patient 8,089 immunoprecipitated an ~70-kD protein as well as the 200-kD and 100-kD proteins (FIG. 1, lane 2). Of note, each of the additional proteins was recognized by no more than 1 of the 16 sera from patients with anti-200/100 autoantibody positivity. Furthermore, none of the additional bands recognized by any of the anti-200/100-kD autoantibody-positive sera corresponded in size to previously recognized myositis-specific autoantigens, including proteins with molecular weights of 72-kD, 54-kD, and/or 21-kD, as seen in patients with anti-signal recognition particle myopathy.

Example 2

Statin Use is Statistically Correlated with Anti-200/100-kD Autoantibody-Positivity Demographic information, laboratory findings, patterns of weakness, thigh magnetic resonance imaging (MRI), and other clinical features of the sixteen anti-200/100-kD autoantibody-positive patients with a necrotizing myopathy were analyzed (Table 1). The single patient having anti-200/100-kD autoantibody specificity a predominantly necrotizing myopathy was excluded from this analysis (Table 1).

TABLE 1

Clinical features of the patients with anti-200/100-kD autoantibodies

| Demographics | |
|---|---|
| Number of patients | 16 |
| Mean age at disease onset (years) | 54 |
| Female sex | 63% |
| White race | 56% |
| Nonwhite race | 44% |
| Deceased | 0% |
| Clinical features | |
| Subjective muscle weakness | 100% |
| Proximal weakness on examination | 100% |
| Wheelchair use | 25% |
| Interstitial lung disease | 0% |
| Malignancy | 13% |
| Raynaud's phenomenon | 13% |
| Rash | 44% |
| Myalgias | 75% |
| Arthralgias | 50% |
| Dysphagia | 63% |
| Statin use | 63% |
| Laboratory findings | |
| Initial creatine phosphokinase level, mean (IU/liter) | 8,702 |
| Maximum creatine kinase level, mean (IU/liter) | 10,333 |
| Antinuclear antibody positive (>1:160) | 6% |
| Elevated erythrocyte sedimentation rate | 38% |
| Elevated C-reactive protein level | 6% |
| Anti-Ro positive | 0% |
| Anti-La positive | 0% |
| Thigh MRI features | |
| Normal findings on thigh MRI | 0% |
| Muscle edema | 100% |
| Atrophy | 75% |
| Fatty replacement | 67% |
| Fascial edema | 25% |
| Electromyography (EMG) findings | |
| Irritable myopathy | 88% |
| Nonirritable myopathy | 13% |
| Normal | 0% |

*Except where indicated otherwise, values are the percent.
CPK = creatine phosphokinase;
CK = creatine kinase;
ANA = antinuclear antibody;
ESR = erythrocyte sedimentation rate;
MRI = magnetic resonance imaging;
EMG = electromyography.

Men and women were represented in roughly equal numbers and had a mean age of 54 years at the onset of disease. All sixteen patients reported previously normal strength, with the acute or subacute onset of muscle weakness occurring in adulthood. At the time of the initial evaluation, all patients had proximal muscle weakness, evidence of muscle edema on bilateral thigh MRI, and markedly elevated creatine kinase levels, with a mean value of 10,333 IU/liter (range 3,052-24,714). Each of the sixteen electromyographs (EMGs) available for review revealed features of myopathy. Fourteen of the sixteen patients (88%) demonstrated an irritable myopathy, while the remaining two myopathies were non-irritable.

Other prominent clinical features included myalgias in 12 (75%) of 16 patients, arthralgias in 8 (50%) of 16 patients, and dysphagia in 10 (63%) of 16 patients. Only 2 (13%) of 16 patients had Raynaud's phenomenon. Although 7 (44%) of 16 patients reported a non-specific rash, no patient had cutaneous features consistent with DM on examination or by historical account. None of these patients had antibodies against extractable nuclear antigens detected by clinical laboratories (including anti-Ro, anti-La, anti-RNP, and anti-Scl-70), and no patient met the criteria for another connective tissue disease. Two patients had prior malignancies: 1 had nonrecurrent ovarian cancer treated 5 years prior to the onset of muscle disease, and the other had prostate cancer that was in clinical remission after treatment.

None of the anti-200/100 autoantibody-positive patients had a family history of muscle disease. Furthermore, scapular winging, facial weakness, asymmetric weakness, or other distinctive features suggestive of inherited muscle disease were absent in each of these patients.

Of note, 10 (63%) of 16 patients had been exposed to statin therapy prior to the onset of weakness. The mean±SD duration of statin treatment prior to the onset of muscle symptoms was 31.3±27.4 months (range 0-84 months). In each case, discontinuing the statin medication did not lead to clear clinical improvement, and the mean±SD length of time between statin discontinuation and muscle biopsy was 5.2±4.6 months (range 1-14 months). A review of the patient records revealed no other potential myotoxin exposures.

To determine whether the association with statin use was coincidental, the frequency of statin use in other groups of patients with myositis was analyzed evaluated (Table 2).

TABLE 2

Frequency of statin use in patients with different forms of muscle disease

| Group | Frequency of statin use | Mean ± SD age of patients (years) |
|---|---|---|
| All patients with anti-200/100-kD antibodies | 10 of 16 (62.5%) | 57.8 ± 14.8 |
| DM patients | 5 of 33 (15.2%)† | 51.0 ± 12.2 |
| PM patients | 7 of 38 (18.4%)† | 49.1 ± 14.1‡ |
| IBM patients | 11 of 31 (35.5%) | 67.7 ± 9.9‡ |
| All patients with anti-200/100-kD antibodies age ≥50 years | 10 of 12 (83.3%) | 64.4 ± 9.2 |
| DM patients age ≥50 years | 4 of 16 (25%)† | 61.0 ± 8.3 |
| PM patients age ≥50 years | 7 of 19 (36.8%)† | 60.4 ± 7.6 |
| IBM patients age ≥50 years | 10 of 30 (33.3%)† | 68.4 ± 9.2 |

DM: dermatomyositis,
PM: polymyositis, and
IBM: inclusion body myositis.
†$P < 0.05$ versus patients having anti-200/100-kD antibodies, by chi-square test.
‡$P < 0.05$ versus patients age ≥50 years having anti-200/100-kD antibodies, by Student's t-test.

5 (15.2%) of 33 patients with DM, 7 (18.4%) of 38 patients with PM, and 11 (35.5%) of 31 patients with IBM had been treated with statins prior to undergoing a muscle biopsy; the frequency of statin use was significantly ($P<0.05$) increased in the anti-200/100 autoantibody-positive group compared with both the DM and PM groups. However, in this analysis, there was no significant difference in statin use between the group of patients with anti-200/100 autoantibody positivity and the group with IBM ($P=0.08$). Because older patients are more likely to be treated with statins, the ages of patients with different forms of myositis was assessed. Compared with all of the anti-200/100 autoantibody-positive patients, who had a mean±SD age of 57.8±14.8 years, the total group of patients with IBM was significantly older, with a mean±SD age of 67.7±9.9 years. When only those patients ages 50 years or older were included in the analysis, 10 (83.3%) of 12 anti-200/100 autoantibody-positive patients, 4 (25%) of 16 patients with DM, 7 (36.8%) of 19 patients with PM, and 10 (33.3%) of 30 patients with IBM had been exposed to statins (Table 2). In this age-matched comparison, statin treatment was significantly increased in the anti-200/100 autoantibody-positive population compared with the DM ($P=0.002$), PM ($P=0.011$), and IBM ($P=0.003$) populations.

There was a striking variation in clinical phenotype, ranging from a chronically intubated, quadriplegic patient to several patients who had only mild weakness. A unique feature in the majority of patients was their relative preservation of strength despite markedly elevated levels of muscle enzymes. However, the medical records of several patients showed an apparent threshold muscle enzyme level (usually between 3,000 and 7,000 IU/liter) above which weakness ensued.

Example 3

The Myopathies Experienced by Anti-200/100-kD Autoantibody-Positive Patients are Responsive to Immunosuppressive Therapy Medication regimens and treatment responses (based on objective improvements in strength) were variable. The clinical characteristics of the 16 anti-200/100 autoantibody-positive patients are available. Of the 14 patients who were followed up longitudinally, 9 (64%) had a complete or near-complete response to immunosuppression, and 5 (36%) had a partial response to immunosuppression. These 5 patients included 1 patient whose progressive muscle weakness was stabilized, but did not improve with immunosuppression. Six (43%) of the 14 patients experienced a relapse when immunosuppressive medication was tapered or withdrawn. Seven (60%) of the 14 patients are currently undergoing tapering of their immunosuppressive medications and have not experienced a relapse to date. Only 1 patient had complete tapering of immunosuppressive medications without experiencing a relapse of weakness.

TABLE 3

Medication regimens and treatment responses of sixteen patients with anti-200/100-kD autoantibodies

| Serum # | Age at onset (years) | Gender | Race | Statin | Highest CPK | Recent CPK | Treatment | Improvement with IS? | Relapse of symptoms with withdrawal of IS? | Duration of IS (months) | Months on Statin before muscle disease onset | Total Months on Statin | Months between statin discontinuation and Muscle Bx |
|---|---|---|---|---|---|---|---|---|---|---|---|---|---|
| 3004 | 59 | M | Non-White | Yes | 24714 | 2908 | P, MTX, RTX, AZA | Near-Complete | Yes | 74 | 39 | 42 | 1 |
| 6031 | 71 | M | White | Yes | 3052 | 55 | P, MTX | Complete | Yes | 36 | 47 | 53 | 2 |
| 7109 | 46 | F | Non-White | No | 11200 | 477 | P, AZA, MMF, MTX, IVIG, CYC, RTX | Partial | Yes | 99 | N/A | N/A | N/A |
| 8001 | 74 | F | White | Yes | 8602 | 309 | P, MTX, AZA | Near-Complete | N/A | 24 | 34 | 41 | 4 |
| 8024 | 33 | F | Non-White | No | 7225 | 7940 | P, AZA, MMF | Near-Complete | Yes | 30 | N/A | N/A | N/A |
| 8040 | 58 | F | Non-White | Yes | 3993 | 895 | P | LTF | Unknown | 2 | 3 | 5 | 9 |
| 8050 | 22 | F | Non-White | No | 17967 | 11120 | P, MTX, IVIG, RTX, MMF | Partial | N/A | 18 | N/A | N/A | N/A |
| 8076 | 71 | M | White | Yes | 8800 | 48 | P, MTX, IVIG | Complete | N/A | 17 | 84 | 85 | 2 |
| 8089 | 48 | F | Non-White | Yes | 17000 | 1225 | P, MTX, RTX | Near-Complete | N/A | 19 | Unknown | Unknown | 11 |
| 8100 | 56 | F | White | Yes | 8000 | 1870 | P, AZA, MMF, MTX, IVIG, FK506, RTX | Near-Complete | Yes | 31 | 12 | 16 | 2 |
| 8109 | 68 | M | White | No | 3275 | 146 | P, HCQ, MTX, IVIG | Partial | Yes | 15 | N/A | N/A | N/A |
| 8126 | 41 | F | Non-White | No | 13506 | 1073 | P, RTX | Complete | N/A | 14 | N/A | N/A | N/A |
| 8130 | 63 | M | White | Yes | 16500 | LTF | P, AZA | LTF | Unknown | 16 | Unknown | Unknown | 1 |
| 8176 | 66 | F | White | Yes | 6000 | 410 | P, AZA, RTX | Partial | N/A | 17 | 0 | 15 | 6 |
| 8209 | 45 | F | White | No | 8500 | 160 | P, MTX, AZA | Near-Complete | No | 21 | N/A | N/A | N/A |
| 8227 | 46 | M | White | Yes | 7000 | 2048 | P, MTX | Partial | N/A | 11 | 31 | 31 | 14 |

P: prednisone;
AZA: azathioprine;
MTX: methotrexate;
IVIG: Intravenous immunoglobulin;
MMF: mycophenylate mofetil;
CYC: cyclosporine;
RTX: rituximab;
FK506: tacrolimus,
HCQ: hydroxychloroquine, and
LTF: lost to follow up.

Most patients had a very modest initial response to prednisone and required combination immunosuppressive therapy. Rituximab and intravenous immunoglobulin were helpful adjuncts when added to prednisone and azathioprine or methotrexate. Most patients required some dose of prednisone for maintenance therapy and reported weakness with steroid tapering, even if their initial response to prednisone was only modest.

Example 4

Necrotizing Myopathy Associated with Anti-200/100-kD Autoantibody Positivity has Features Characteristic of Immune-Mediated Myopathies Sixteen (94%) of 17 patients with anti-200/100 autoantibodies had muscle biopsy specimens showing prominent myofiber necrosis; the remaining patient's biopsy specimen was notable for extensive inflammatory infiltrates, and a subsequent analysis did not include the results of this biopsy. Although close examination revealed endomysial and/or perivascular collections of inflammatory cells in 5 (31%) of the 16 muscle biopsy specimens, the degree of inflammation was mild compared with that seen in typical muscle biopsy specimens obtained from patients with PM or DM. No biopsy specimen obtained from a patient with anti-200/100 autoantibody positivity revealed evidence of more than mild denervation, and no biopsy specimen was positive for abnormal glycogen accumulation or amyloid deposition.

Figure 2:
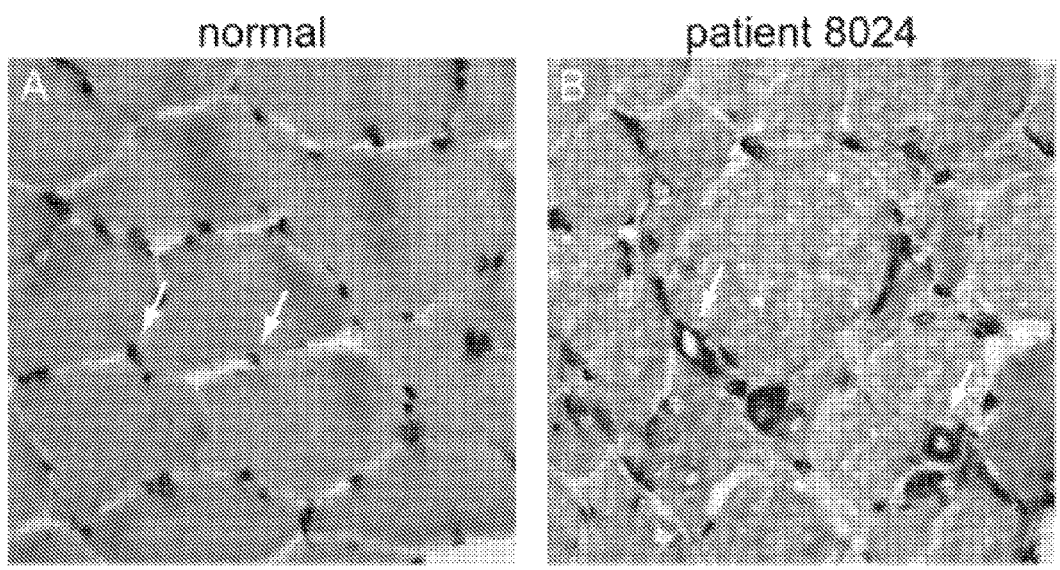
FIGS. 2A and 2B include photomicrographs showing capillary morphology of muscle biopsy specimens obtained from a normal donor (FIG. 2A) and a patient (patient 8024) with anti-200/100 autoantibodies (FIG. 2B). Specimens were stained with anti-CD31, an endothelial cell marker. Arrows indicate endomysial capillaries with normal morphologic features in the control specimen (FIG. 2A) and those with thickened walls and dilated lumens in the patient with anti-200/100 autoantibodies (FIG. 2B). These biopsy specimens were processed simultaneously under identical conditions (original magnification ×40).

Of the 16 patients with necrotizing myopathies who were anti-200/100 autoantibody positive, frozen muscle tissue samples obtained from 8 patients were available for further analysis. To assess blood vessel morphology, sections were stained with anti-CD31 antibodies. Abnormally enlarged endomysial capillaries with thickened walls were observed in 5 (63%) of 8 biopsy specimens (arrows in FIG. 2B). However, the density of capillaries within muscle tissue was not noticeably reduced in any of the muscle biopsy specimens.

Figure 3:
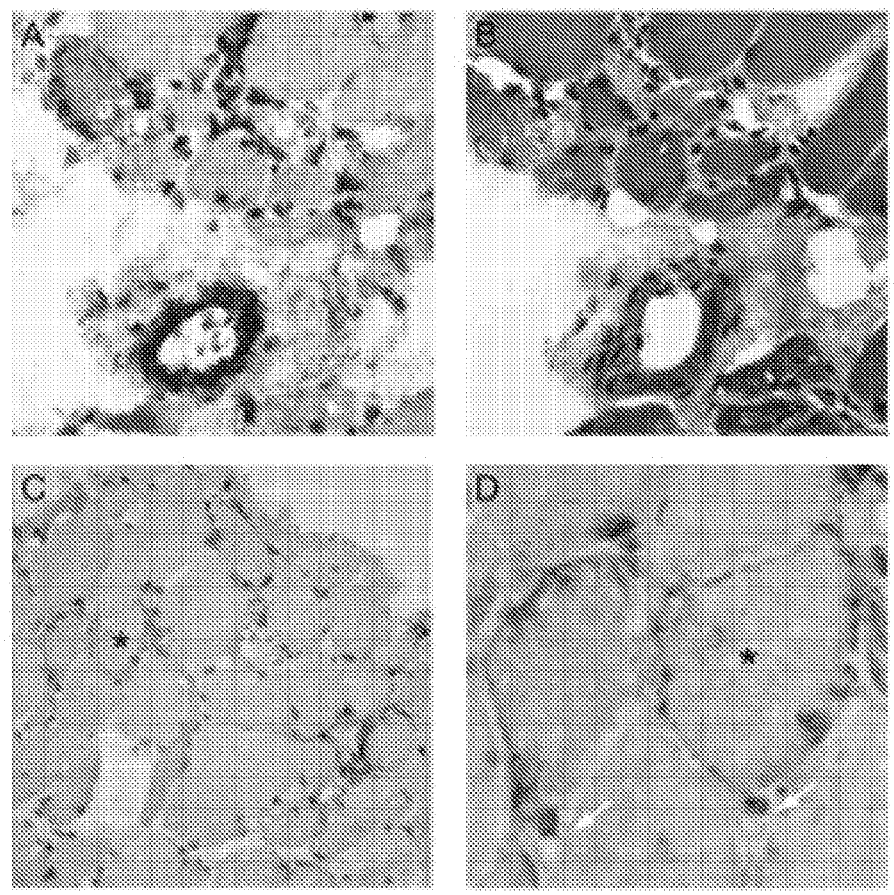
FIG. 3 shows a higher-magnification view of the field shown in FIG. 3C.

Complement deposition was evaluated by staining the available anti-200/100 autoantibody-positive muscle biopsy specimens with antibodies recognizing the membrane attack complex. Although endomysial capillaries were not definitively recognized by the antibody (FIG. 3D), in 6 (75%) of 8 muscle biopsy specimens, small perimysial vessels were stained (FIGS. 3A and 3B). In contrast, blood vessels from control muscle biopsy specimens did not stain intensely with membrane attack complex antibodies. As expected, membrane attack complex deposition was also present on necrotic and degenerating myofibers; this was considered a nonspecific finding. However, in 4 (50%) of 8 of the anti-200/100 autoantibody-positive muscle biopsy specimens, the sarcolemmal surfaces of scattered, non-necrotic muscle fibers stained positive for membrane attack complex (FIGS. 3C and D); as shown, some of these muscle cells were relatively small, suggesting they could be regenerating fibers.

Figure 4:
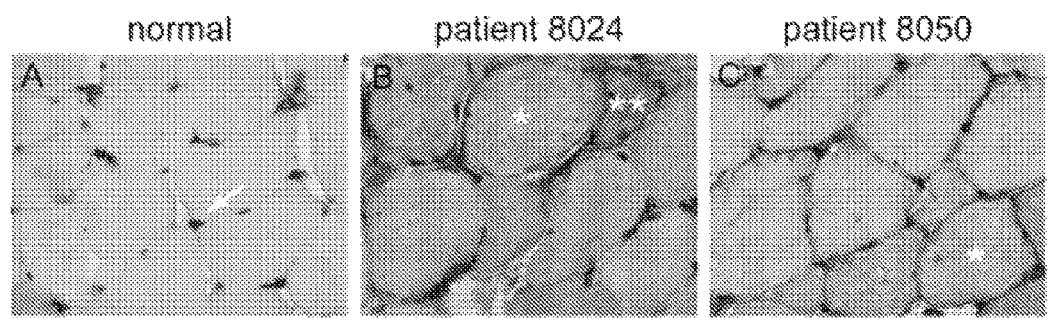
FIGS. 4A-C include photomicrographs showing class I major histocompatibility complex (MHC) deposition on non-necrotic fibers in biopsy specimens obtained from anti-200/100 autoantibody-positive patients.

Staining of anti-200/100 autoantibody-positive muscle biopsy specimens with antibodies recognizing class I MHC showed that the sarcolemma of 4 (50%) of 8 specimens were clearly class I MHC positive (FIG. 4). Several others had borderline class I MHC staining, but this appeared markedly less intense than that seen in muscle biopsy specimens from Jo-1-positive patients with PM that were included as positive controls in the same experiment.

The autoimmune myopathies (referred to collectively as myositis) are a family of conditions characterized clinically by symmetric proximal muscle weakness, elevated serum creatine kinase levels, and myopathic findings on electromyography (Dalakas M C, et al., *Lancet* 2003; 362:971-82 and Mammen A L. *Ann N Y Acad Sci* 2010; 1184:134-53). Although other muscle conditions can cause similar clinical syndromes, diagnosing an autoimmune disorder carries important therapeutic and prognostic implications, because only these disorders routinely respond to immunosuppressive therapy.

As with other systemic autoimmune diseases, a strong association of autoantibodies with distinct clinical phenotypes is observed in patients with autoimmune myopathy. For example, autoantibodies directed against aminoacyl-transfer RNA (tRNA) synthetases are the most frequent myositis-specific autoantibodies (MSAs) and are observed in ~20% of patients with myositis (Targoff I N, et al., *Rheum Dis Clin North Am* 2002; 28:859-90, viii). These and autoantibodies recognizing other tRNA synthetases are associated with a specific constellation of clinical features including interstitial lung disease, Raynaud's phenomenon, arthritis, and a characteristic cutaneous finding known as mechanic's hands (Yoshida S, et al., *Arthritis Rheum* 1983; 26:604-11; Marguerie C, et al., *Q J Med* 1990; 77:1019-38). Although autoantibody screening can play a significant role in the diagnosis of immune-mediated muscle disease, such antibodies are not always observed.

The presence of inflammatory infiltrates in muscle biopsy specimens is another well-recognized feature of the autoimmune myopathies (Dalakas M C, et al., 2003). However, muscle biopsy specimens from some patients with autoimmune myopathies contain few, if any, inflammatory cell infiltrates. For example, patients with myositis-specific autoantibodies (MSAs) directed against components of the SRP have biopsy samples that are notable for degenerating, necrotic, and regenerating muscle cells without extensive inflammatory cell infiltrates (Miller T, et al., *J Neurol Neurosurg Psychiatry* 2002; 73:420-8; Kao A H, et al., *Arthritis Rheum* 2004; 50:209-15; Hengstman G J, et al., *Ann Rheum Dis* 2006; 65:1635-8; and Dimitri D, et al., *Muscle Nerve* 2007; 35:389-95). Consequently, it is likely that patients with otherwise undiagnosed necrotizing myopathies might also have unique autoantibodies that could be used for diagnosis.

Among a group of 225 patients with myopathies, thirty-eight had muscle biopsy specimens with predominantly necrotizing myopathies. After extensive laboratory testing, specific conditions could be diagnosed in twelve of these patients; these were largely patients with anti-signal recognition particle (anti-SRP) or antisynthetase myositis. The sera of the remaining twenty-six patients were screened for the presence of novel autoantibodies and observed that sixteen of these sera immunoprecipitated a pair of proteins with approximate molecular weights of 200 kD and 100 kD, respectively. In addition, among the other 187 patients, one patient with a biopsy specimen showing abundant inflammatory cell infiltrates shared this immunospecificity. The patients with anti-200/100-kD autoantibodies did not have other known autoantibodies, including anti-SRP. Thus, anti-200/100-kD autoantibodies characterize a unique subset of patients with myopathies, representing sixteen of the twenty-six patients (62%) with idiopathic necrotizing myopathies.

In many respects, the clinical features of patients with the anti-200/100-kD autoantibody immunospecificity are similar to those of patients with other forms of immune-mediated myopathy; both groups typically experienced the subacute onset of proximal muscle weakness with elevated creatine kinase levels, had findings of irritable myopathy on electromyography, evidence of edema on MRI, and, in most cases, a clear response to immunosuppressive therapy. However, there were several unique features of the anti-200/100-kD autoantibody-positive patients. First, several patients had very high creatine kinase levels (in the range of 3,000-8,000 IU/liter) but only minimal muscle weakness. This indicates that either an unusual capacity of these patients to regenerate muscle with sufficient efficiency to keep pace with extensive muscle destruction or that these patients have a muscle membrane abnormality that allows leakage of creatine kinase without causing weakness; such an abnormality could be consistent with the finding of membrane attack complex deposition on the sarcolemma of non-necrotic muscle fibers. Second, in >60% of these patients, exposure to statin therapy preceded the development of muscle symptoms, which persisted long after treatment with the myotoxin was discontinued. Importantly, this association was strongest in older patients; more than 80% of anti-200/100 kD autoantibody-positive patients ages 50 years or older had been exposed to statins. This rate was significantly higher than the rates of statin treatment in age-matched groups of patients with polymyositis, dermatomyositis, or inclusion body myositis.

Although the anti-200/100-kD autoantibody-positive patients share certain features with the well-described populations of patients with anti-SRP antibodies, two key findings distinguish these groups as distinct. First, sera from patients with anti-200/100-kD autoantibodies did not recognize any of the signal recognition particle subunits, and sera from patients with anti-SRP autoantibodies did not recognize proteins with molecular weights of ~200 kD or ~100 kD. These observations demonstrate that patients with the anti-200/100-kD autoantibody specificity are immunologically distinct from the population of patients with anti-SRP antibodies. Second, several anti-200/100 autoantibody-positive patients who had extremely high CK levels had only minimal weakness. This was unusual because patients with anti-SRP antibodies with high CK levels are typically uniformly very weak.

To further characterize the muscle disease in patients with anti-200/100 autoantibodies, muscle biopsy specimens were stained with antibodies against membrane attack complex, endothelial cell markers, and class I MHC. Membrane attack complex deposition represents the end-stage of the complement cascade and may indicate that the tissue is targeted for destruction by the immune system. The deposition of membrane attack complex on endomysial capillaries has been shown in patients with dermatomyositis (Kissel J T et al., *N Engl J Med* 1986; 314:329-34 and Emslie-Smith A M et al., *Ann Neurol* 1990; 27:343-56) and in three of four analyses of biopsy specimens positive for anti-SRP (Miller T, et al., 2002; Kao A H, et al., 2004; Hengstman G J, et al., 2006; and Dimitri D, et al., 2007); this does not occur in muscular dystrophies (Spuler S et al., *Neurology* 1998; 50:41-6.). Although membrane attack complex deposition was not observed on endomysial capillaries in biopsy specimens obtained from patients with anti-200/100-kD autoantibodies, in five of eight specimens, endomysial capillaries were abnormally thickened and enlarged. Similar morphologic abnormalities have been described both in patients with anti-SRP antibodies and in a group of patients with "necrotizing myopathy with pipestem capillaries." Although the latter group shares some pathologic features with patients with anti-200/100-kD autoantibodies and anti-SRP antibodies, these patients differed by having either another connective tissue disease or active cancer (Emslie-Smith A M and Engel A G, *Neurology* 1991; 41:936-9).

Despite its absence on capillaries, membrane attack complex deposition in small perimysial blood vessels was evident in six (75%) of eight biopsy specimens obtained from patients with anti-200/100-kD autoantibodies. Without being bound to theory, it is reasonable that deposition of complement in these cases may reflect a novel vascular target in this patient population. In addition, membrane attack complex localized to the surface of non-necrotic fibers was noted in 4 (50%) of the 8 biopsy specimens from patients with anti-200/100 autoantibodies that were analyzed. Although the presence of membrane attack complex on non-necrotic fibers have previously been reported in immune-mediated myopathies (Oxenhandler R, et al., *Hum Pathol* 1982; 13:745-57), this is not a general feature of these disorders; in multiple studies of anti-SRP myopathy, membrane attack complex was observed on non-necrotic fibers in only one of seven (Miller T, et al., *J Neurol Neurosurg Psychiatry* 2002; 73:420-8), none of six (Hengstman G J, et al., 2006), and one of three (Dimitri D, et al., *Muscle Nerve* 2007; 35:389-95) muscle biopsy specimens. It should be noted that membrane attack complex deposition on non-necrotic myofibers has also been reported to occur in some dystrophies (Spuler S, et al., Neurology 1998; 50:41-6), and that membrane attack complex deposition on blood vessels and muscle fibers may be secondary to membrane damage rather than a primary pathologic event.

Finally, four of the eight available biopsy specimens included myofibers with sarcolemmal class I MHC staining. This is a characteristic feature of immune-mediated myopathies and is rare or absent in biopsy specimens from patients with muscular dystrophies and other muscle and nerve disorders (Van der Pas J, et al., *J Neurol Neurosurg Psychiatry* 2004; 75:136-9 and Sundaram C, et al., *Neurol India* 2008; 56:363-7). By comparison, results of studies evaluating class I MHC staining in patients with antibodies to SRP have been mixed; one study noted class I MHC-positive fibers in two of three patients (Dimitri D, et al., 2007), a second study showed these fibers in three of six patients (Miller T, et al., *J Neurol Neurosurg Psychiatry* 2002; 73:420-8), and a third study showed the fibers in none of six patients (Hengstman et al, 2006).

Interestingly, two recent reports describe patients in whom a necrotizing myopathy developed during statin treatment and progressed despite discontinuation of the myotoxic medication (Needham, et al., *Neuromuscul Disord* 2007; 17: 194-200 and Grable-Esposito et al., *Muscle Nerve* 2010; 41:185-90). In the larger of the two reports, Grable-Esposito et al., described twenty-five patients who experienced the development of an apparently immune-mediated, statin-associated necrotizing myopathy that shares many of the clinical features observed in our cohort of anti-200/100-kD autoantibody-positive patients. For example, this group of patients had proximal muscle weakness, included men and women in almost equal numbers, had a mean creatine kinase level of 8,203 IU/liter, required multiple immunosuppressive medications to achieve improved strength, and experienced a relapse upon tapering of immunosuppressive medications. The muscle biopsy specimens from eight similar patients were analyzed in detail by Needham and colleagues (Needham, et al., 2007). Whereas all of the biopsy specimens described in Needham, et al., had increased class I MHC expression on the surface of non-necrotic muscle fibers, only four of the eight anti-200/100-kD autoantibody-positive patients described herein were positive for class I MHC staining.

In conclusion, the results reported herein above identify a group of patients with a necrotizing myopathy and a novel anti-200/100 autoantibody specificity. Interestingly, development of this phenotype is associated with exposure to statin medications. In addition to the presence of auto-antibodies, all of the patients responded to immunosuppression, and many experienced a flare of weakness when this treatment was tapered. These findings tend to indicate the presence of an immune-mediated myopathy in these subjects. The presence of class I MHC on the surface of non-necrotic fibers also supports that this process is immune-mediated. Indeed, those patients with necrotizing myopathies and anti-200/100 autoantibodies most likely have an autoimmune disease that should be treated with immunosuppressive medication.

Example 5

Up-Regulation of 200-kd and 100-kd Autoantigen Expression by Statins

As reported herein above, sera from a group of patients with IMNM immunoprecipitate ~200-kd and ~100-kd proteins from radio-labeled HeLa extracts.

Figure 5:
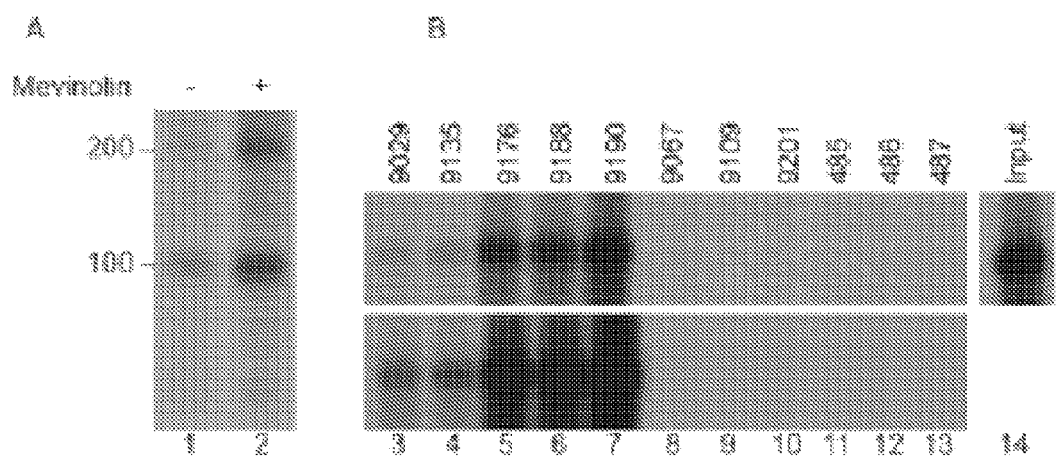
FIGS. 5A and 5B include autoradiographs (FIG. 5A) showing up-regulated expression of the 200-kD and 100-kD autoantigens by statins and (FIG. 5B) identification of the 100-kD autoantigen as 3-hydroxy-3-methylglutaryl-coenzyme A reductase (HMG-CoA reductase). Radiolabeled lysates generated from HeLa cells treated for twenty-four hours in the absence (lane 1) or presence (lane 2) of 10 µM mevinolin were immunoprecipitated with patient serum 9190, as described herein below.

Given the strong association of statin use with the development of these anti-200/100-kd autoantibodies, HeLa cells were labelled with $^{35}$S-methionine/cysteine after pretreatment for 24 hours with either 10 pM mevinolin or vehicle (DMSO) alone. To validate the protein equivalence of these lysates, immunoprecipitations were performed using antibodies against Mi-2 or PM-Scl. As anticipated, equal amounts of Mi-2 and the 5 protein components of the PM-Scl complex were detected in each lysate type. In contrast, 3-fold-increased levels of both the 200-kd and the 100-kd protein were immunoprecipitated from the mevinolin-treated cells, demonstrating that levels of these autoantigens are up-regulated by statins (FIG. 5A).

Goldstein and Brown (Goldstein J L and, Brown M S. Nature 1990; 343:425-30) originally demonstrated that the expression of 3-hydroxy-3-methylglutaryl-coenzyme A reductase (abbreviated as HMG-CoA reductase or as HMGCR) is up-regulated by statin treatment. Morikawa and colleagues (Morikawa S et al., J Atheroscler Thromb 2005; 12:121-31) extended these findings to muscle cells. They used DNA microarray analysis to demonstrate that statins induce the expression of nineteen genes in a human skeletal muscle cell line, most of which are related to cholesterol biosynthesis. Among these, HMG-CoA reductase was selected as a candidate for the 100-kD autoantigen because of its 97-kd molecular weight.

$^{35}$S-methionine-labeled HMGCR was generated by (IVTT) and used in an immunoprecipitation assay with serum from 16 patients with anti-200/100-kd autoantibodies, as well as serum from 6 negative control subjects, consisting of 3 DM patients and 3 normal individuals without statin exposure. Serum samples from anti-200/100-kd-positive patients immunoprecipitated HMGCR, whereas serum samples from the control groups did not (FIG. 5B).

Example 6

Figure 6:
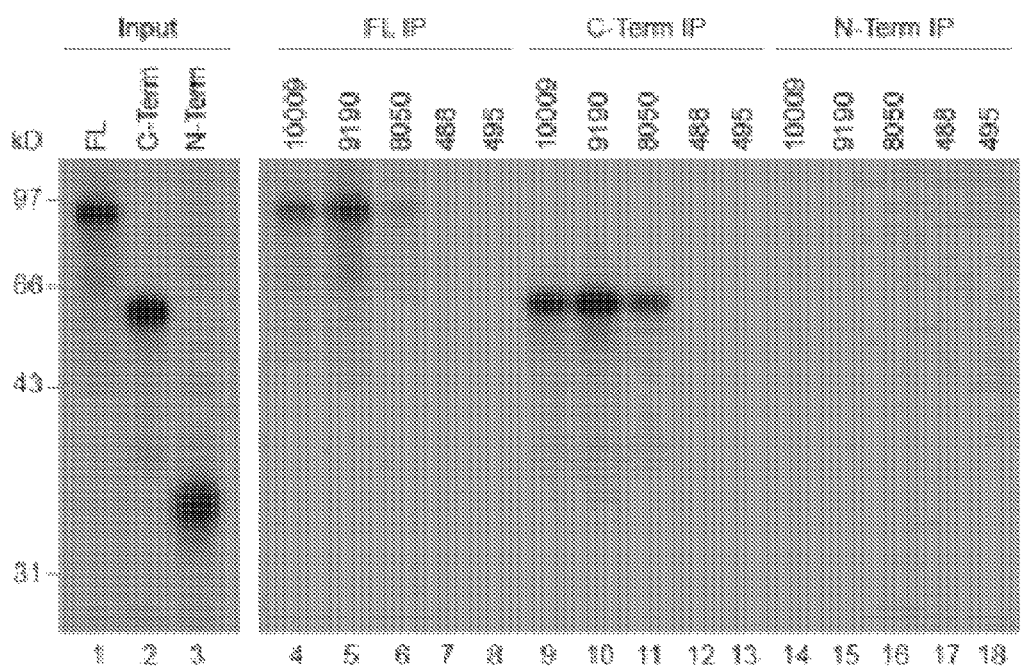
FIG. 6 is an autoradiograph showing results of an immunoprecipitation (IP) of full-length 3-hydroxy-3-methylglutaryl-coenzyme A reductase (HMGCR) and a piece corresponding to the C-terminus (amino acids 340-888) by human anti-HMGCR antibodies. Immunoprecipitations were performed using 3 different $^{35}$S-methionine-labeled HMGCR products: full-length (FL; lanes 4-8), C-terminus (C-term; lanes 9-13), and N-terminus (N-term; lanes 14-18). Serum samples 10009, 9190, and 8050 are from anti-200/100-kd-positive patients; samples 488 and 495 are from normal control subjects. Input in vitro transcription/translated (IVTT) products are shown in lanes 1-3; in each case, 0.4 times the amount used for the immunoprecipitation was used. Results are representative of 2-8 separate experiments. Molecular weight markers are shown at the left.
Figure 7:
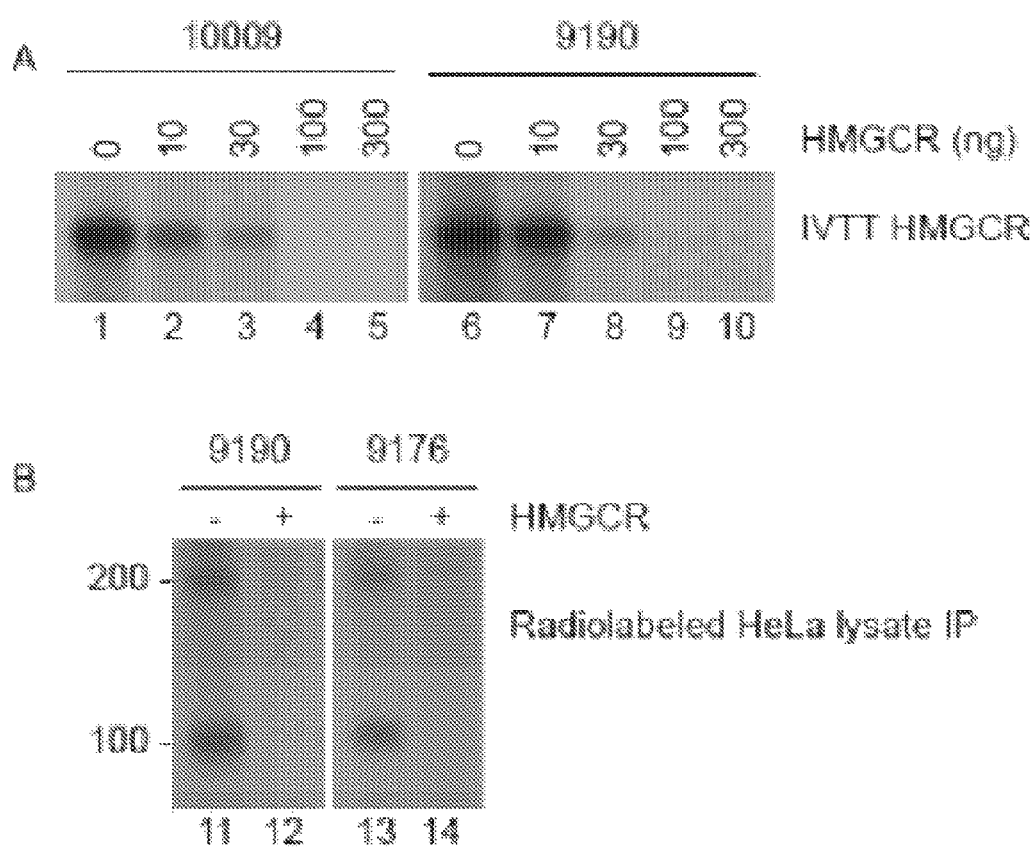
FIGS. 7A and 7B include three autoradiographs.

The Anti-200/100-kD-Autoantibodies Recognize a C-Terminal Fragment of HMG-CoA Reductase HMG-CoA reductase is a membrane protein with a small extracellular domain, seven membrane-spanning domains, and an intracellular catalytic domain. To define the region(s) of the protein recognized by sera from patients with anti-HMGCR antibodies, $^{35}$S-methionine-labeled full-length HMGCR protein, an N-terminal fragment including the extracellular and membrane-spanning domains (aa 1-377), and a C-terminal fragment including the intracellular portion of the molecule (aa 340-888) were synthesized. Serum from anti-HMGCR-positive patients consistently immunoprecipitated full-length HMGCR and the C-terminal fragment, but not the N-terminal fragment (FIG. 6). When anti-HMGCR-positive sera were preincubated with increasing concentrations of unlabeled C-terminal HMGCR prior to immunoprecipitation of $^{35}$S-methionine-labeled full-length HMGCR protein, immunoprecipitation was abolished (FIG. 7A). Taken together, these findings demonstrate that anti-HMGCR autoantibodies recognized the intracellular C-terminal portion of this enzyme.

Example 7

No Recognition of the 200-kd Protein by a Unique Autoantibody

To determine whether serum from anti-HMGCR-positive patients includes distinct autoantibodies that recognize the 200-kd protein, immunoprecipitations from $^{35}$S-methionine-labeled, mevinolin-treated HeLa cell extracts, again preincubating with purified C-terminal HMGCR protein, were performed (FIG. 7B). This procedure inhibited the immunoprecipitation of both HMGCR and the –200-kD protein, suggesting that the –200-kD protein is either coimmunoprecipitated with HMGCR or is an HMGCR dimer.

Example 8

Validation of a new ELISA for the Detection of Anti-HMGCR Autoantibodies in Patient Sera To screen patients rapidly for anti-HMGCR autoantibodies, an ELISA was developed. A serum sample was defined as being positive for anti-HMGCR if the relative absorbance value was 3 standard deviations or higher than the mean value in 20 healthy control subjects who had never taken statins. Using this method, all 16 of the anti-200/100-kd-positive serum samples previously identified by immunoprecipitation from HeLa cell extracts were found to be anti-HMGCR positive. In contrast, none of 33 patients with DM (including 5 who had previously taken statins) and none of 31 patients with IBM (including 11 who had previously taken statins) were anti-HMGCR positive.

Next, the HMGCR ELISA was used to screen serum samples from all 750 patients enrolled in a longitudinal study of patients at the Johns Hopkins Myositis Center between May 2002 and April 2010. Of these, 45 patients (6%) were anti-HMGCR positive by ELISA (Table 4).

TABLE 4

Clinical features of the 45 patients who were positive for anti-HMGCR by ELISA*

| Serum | Statin use | HMGCR ELISA | Age at onset (years) | Sex | Race | Highest CK | Proximal Weakness | EMG | Muscle biopsy | rs4149056 genotype |
|---|---|---|---|---|---|---|---|---|---|---|
| 07039 | No | 0.969 | 49 | M | B | 20,000 | Yes | Not done | N + I | |
| 07056 | No | 0.749 | <40 | F | W | 6,323 | Yes | IM | NM | |
| 07090 | No | 1.304 | 57 | M | W | 10,310 | Yes | IM | NM | |
| 08024 | No | 1.123 | 32 | F | B | 7,225 | Yes | NIM | NM | |
| 08038 | No | 0.347 | 36 | M | W | 4,071 | Yes | NIM | N + I | |
| 08050 | No | 1.260 | 21 | F | B | 17,967 | Yes | IM | NM | |
| 08109 | No | 0.849 | 68 | M | W | 3,275 | Yes | IM | NM | |
| 08126 | No | 1.378 | 40 | F | A | 13,506 | Yes | IM | N + I | TT |
| 08196 | No | 1.524 | 42 | F | B | 35,000 | Yes | IM | Not done | TT |
| 08209 | No | 0.947 | 45 | F | W | 8,500 | Yes | IM | NM | CT |
| 09029 | No | 0.765 | 4 | F | B | 16,000 | Yes | NIM | NM | TT |
| 09063 | No | 0.982 | 20 | F | W | 2,000 | Yes | n/a | N + I | |

TABLE 4-continued

Clinical features of the 45 patients who were positive for anti-HMGCR by ELISA*

| Serum | Statin use | HMGCR ELISA | Age at onset (years) | Sex | Race | Highest CK | Proximal Weakness | EMG | Muscle biopsy | rs4149056 genotype |
|---|---|---|---|---|---|---|---|---|---|---|
| 09088 | No | 0.629 | 47 | F | B | 22,733 | Yes | IM | n/a | |
| 10029 | No | 0.924 | 16 | F | A | 16,000 | No | Normal | NM | |
| 09184 | No | 1.759 | 38 | M | W | 17,976 | Yes | IM | N + I | |
| 03004 | Yes | 1.259 | 58 | M | B | 24,714 | Yes | IM | NM | TT |
| 05017 | Yes | 1.228 | 54 | M | W | 13,600 | Yes | Not done | NM | |
| 06031 | Yes | 0.718 | 71 | M | W | 3,052 | Yes | IM | NM | |
| 06061 | Yes | 0.547 | 54 | F | W | 15,000 | Yes | IM | NM | |
| 07054 | Yes | 0.355 | 43 | M | W | 11,427 | Yes | IM | N + I | |
| 07094 | Yes | 0.948 | 48 | F | W | 200 | Yes | n/a | Not done | |
| 07109 | Yes | 0.942 | 44 | F | A | 11,200 | Yes | NIM | NM | |
| 08001 | Yes | 0.242 | 75 | F | W | 8,602 | Yes | IM | NM | |
| 08040 | Yes | 1.159 | 57 | F | B | 3,993 | Yes | IM | NM | |
| 08076 | Yes | 1.259 | 70 | M | W | 8,800 | Yes | IM | NM | CC |
| 08089 | Yes | 0.768 | 47 | F | B | 17,000 | Yes | IM | NM | TT |
| 08100 | Yes | 0.378 | 57 | F | W | 8,000 | Yes | IM | NM | |
| 08130 | Yes | 0.751 | 62 | M | W | 16,500 | Yes | IM | NM | |
| 08144 | Yes | 0.287 | 65 | M | W | 254 | No | Not done | Not done | |
| 08145 | Yes | 1.411 | 54 | F | W | 17,000 | Yes | IM | NM | |
| 08148 | Yes | 0.608 | 65 | M | W | 5,800 | Yes | n/a | N + I | |
| 08176 | Yes | 1.142 | 66 | F | W | 6,000 | Yes | IM | NM | TT |
| 08227 | Yes | 0.966 | 49 | M | W | 7,000 | Yes | NIM | NM | |
| 09125 | Yes | 0.517 | 56 | F | W | 1,876 | Yes | NIM | N + I | |
| 09135 | Yes | 0.746 | 58 | F | W | 3,000 | Yes | NIM | NM | TT |
| 09153 | Yes | 1.273 | 65 | M | W | 4,197 | Yes | IM | NM | TT |
| 09170 | Yes | 0.556 | 80 | F | W | 1,200 | Yes | NIM | NM | |
| 09172 | Yes | 1.495 | 53 | F | W | 6,840 | Yes | IM | NM | TT |
| 09176 | Yes | 1.000 | 70 | M | W | 8,800 | Yes | IM | NM | TT |
| 09188 | Yes | 1.996 | 65 | M | W | 4,065 | Yes | IM | NM | CT |
| 09190 | Yes | 1.486 | 49 | F | W | 3,700 | Yes | n/a | NM | TT |
| 10009 | Yes | 0.736 | 66 | M | W | 5,000 | Yes | NIM | NM | TT |
| 10044 | Yes | 1.810 | 62 | M | W | 11,600 | Yes | IM | N + RV | TT |
| 10062 | Yes | 0.292 | 60 | F | W | 4,000 | Yes | n/a | n/a | TT |
| 10072 | Yes | 1.169 | 54 | F | W | 4,000 | Yes | IM | NM | |

*Absorbance values listed in the "HMGCR ELISA" column, are in units relative to the absorbance of an arbitrary positive control sample (sample 9176). The cutoff value for a positive result in the enzyme-linked immunosorbent assay (ELISA) for HMG-CoA reductase (HMGCR) antibodies was 0.215 absorbance units; this value equated to three standard deviations above the mean for twenty healthy subjects who had never taken statins. Statin use represents the period prior to serum testing. Creatine kinase (CK) values are expressed as IU/liter. Electromyography (EMG) findings were categorized as normal, irritable myopathy (IM), or nonirritable myopathy (NIM). Muscle biopsy findings were categorized as necrosis plus inflammation (N + I), necrotizing myopathy (NM), or necrosis plus rimmed vacuoles (N + RV). Genotyping for rs4149046 was performed on seventeen anti-HMG-CoA reductase-antibody positive patients for whom DNA samples were available.
n/a = not applicable.
W = WHITE,
B = BLACK,
A = ASIAN To validate the ELISA, ELISA and IVTT immunoprecipitation data obtained using a subset of sera from this cohort that were collected from 307 consecutive unique patients between January 2009 and April 2010 was compared. In this subgroup, 17 anti-HMGCR-positive patients were identified by both methods. The ELISA identified 1 additional anti-HMGCR-positive serum that was negative by immunoprecipitation (serum 10029). Since this patient had a necrotizing myopathy with elevated CK levels, this was determined to be a true anti-HMGCR-positive serum and not a false-positive serum. These results demonstrate a very high correlation between these 2 methods and validate the ELISA test as a reliable, efficient screen for detecting anti-HMGCR autoantibodies.

Example 9

Clinical Features of Anti-HMGCR-Positive Patients

Of the 45 anti-HMGCR-positive patients, 30 (66.7%) had previously taken statins (Table 1). Among the 26 patients who presented to our clinic at age 50 years or older, 24 had taken statins (92.3%). Thus, the prevalence of statin use in patients with anti-HMGCR autoantibodies is significantly higher than what we and others have previously reported in age-matched patients with other myopathies (ages ~50 years), including DM (25%), PM (36.8%), and IBM (33.3%) (Grable-Esposito et al., 2010 and Christopher-Stine et al., 2010).

Anti-HMGCR-positive patients were characterized by proximal muscle weakness (95.6%), elevated CK levels (mean±SD 9,718±7,383 IU/liter), and myopathic findings on EMG (97.3%) (Table 2). All of the 40 available muscle biopsy samples (100%) were reported to have prominent degenerating, regenerating, and/or necrotic fibers. Significant inflammatory infiltrates were noted in 8 of 40 muscle biopsy samples (20%) and rimmed vacuoles were visualized in 1 of 40 biopsy specimens (2.5%); this patient had predominantly proximal muscle weakness and did not have clinical features typical of IBM. Patients who had not taken statins were clinically indistinguishable from those who had, except for their younger age (mean±SD 37±17 years versus 59±9 years), higher CK levels (13,392±8,839 versus 7,881±5,875 IU/liter), and race (46.7% versus 86.7% white) (Table 5).

TABLE 5

Clinical features of the forty-five anti-HMG-CoA reductase-autoantibody positive patients*

| | All patients | | Statin-naive Patients | | Statin-exposed patients | | |
|---|---|---|---|---|---|---|---|
| | # (%) of patients[†] | Total # assesse | # (%) of patients[†] | Total # assesse | # (%) of patients[†] | Total # assessed | P[‡] |
| White | 33 (73.3) | 45 | 7 (46.7) | 15 | 26 (86.7) | 30 | 0.012 |
| Male | 19 (42.2) | 45 | 5 (33.3) | 15 | 14 (46.7) | 30 | NS |
| Myopathy on EMG | 36 (97.3) | 37 | 12 (92.3) | 13 | 24 (100) | 24 | NS |
| Irritable | 27 (72.9) | 37 | 9 (69.2) | 13 | 18 (75) | 24 | NS |
| Nonirritable | 9 (24.3) | 37 | 3 (23.1) | 13 | 6 (25) | 24 | NS |
| Proximal weakness | 43 (95.6) | 45 | 14 (93.3) | 15 | 29 (96.7) | 30 | NS |
| Necrosis on biopsy | 40 (100) | 40 | 13 (100) | 13 | 27 (100) | 27 | NS |
| Inflammation on | 8 (20) | 40 | 5 (38.5) | 13 | 3 (11.1) | 27 | 0.11 |
| Age (years) | 52 ± 16 | 45 | 37 ± 17 | 14 | 59 ± 9 | 30 | <0.0001 |
| Creatine kinase levels | 9,718 ± 7,383 | 45 | 13,392 ± 8,839 | 15 | 7,881 ± 5,875 | 30 | 0.0164 |

*NS = not significant; EMG = electromyography.
[†]Age and creatine kinase levels are reported as the mean ± standard deviation.
[‡]Statin-exposed versus statin-naive patients.

While 43 of 45 anti-HMGCR-positive patients had no other systemic autoimmune disease (95.6%), patient 8196 had Jo-1 antibodies and interstitial lung disease. Another patient (patient 8038) had scleroderma, anti-PM-Scl antibody, and interstitial lung disease. Neither of these patients had taken statins prior to developing muscle symptoms.

The vast majority of anti-HMGCR-positive patients had clinical features consistent with an immune-mediated myopathy. However, a single patient (patient 8144) presented with only persistent myalgias after statin use, normal subjective and objective muscle strength, unremarkable findings on MRI of both thighs, normal findings on EMG, and a CK level of only 254 IU/liter. This patient's HMGCR ELISA result were less than 3-standard deviations above the mean of 2000 normal controls. Therefore, his patient should be monitored for signs of muscle weakness and/or development of HMGCR autoantibodies.

Example 10

No Increased Prevalence of the Single-Nucleotide Polymorphism Associated with Statin Myopathyin Anti-HMGCR-Positive Patients A recent study published by the Study of the Effectiveness of Additional Reductions in Cholesterol and Homocysteine (SEARCH) Collective (*N Engl J Med* 2008; 359: 789-99) demonstrated that the presence of a specific polymorphism in the SLCO1B1 gene (i.e., the rs4149056 C allele) is strongly associated with the development of statin myopathy. This gene encodes the organic anion-transporting polypeptide OATP-1B1, which regulates the hepatic uptake of statins. While the prevalence of the C allele in their population of ~12,000 participants (mostly of European ancestry) was 0.15, its prevalence in those who developed a statin myopathy within 1 year of starting simvastatin at a dosage of 80 mg/day was 0.54.

DNA samples were available from 17 of the anti-HMGCR-positive patients, and the frequency of the rs4149056 C allele in this population was 0.12. When the 6 patients who had not taken statins and/or were of non-European ancestry were excluded, the prevalence of the C allele in the remaining 11 patients was 0.14. Although the number of subjects genotyped was small, the prevalence of the rs4149056 C allele in these anti-HMGCR-positive patients is consistent with the range of 0.14-0.22 previously reported among those of European ancestry (SEARCH Collaborative Group, *N Engl J Med* 2008; 359: 789-99)

Example 11

Figure 8:
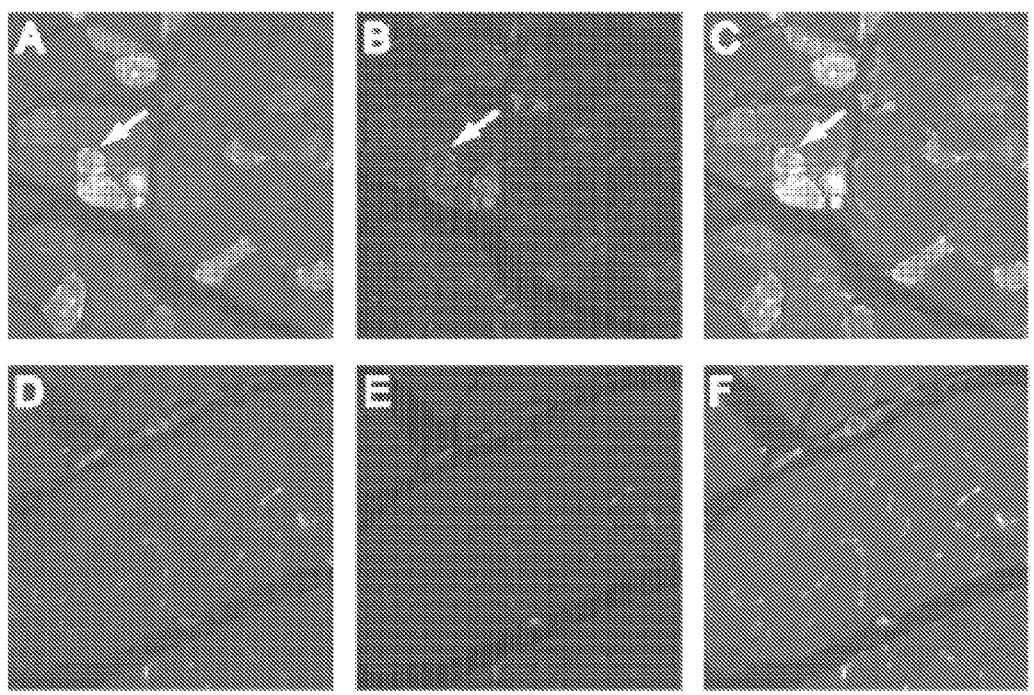
FIGS. 8A-8F include photomicrographs showing up-regulation of HMG-CoA reductase expression in regenerating myofibers expressing neural cell adhesion molecule (NCAM). Muscle biopsy samples from anti-HMGCR-positive patients (FIGS. 8A-8C) and control subjects (FIGS. 8D-8F) were costained with anti-NCAM antibodies (green) (FIGS. 8A and 8D), anti-HMGCR antibodies (red) (FIGS. 8B and 8E), and DAPI (blue) to stain nuclei. Overlay images (FIGS. C and F) demonstrate that HMGCR and NCAM are frequently coexpressed at high levels in the same myofibers in anti-HMGCR-positive muscle biopsy tissues (arrows), but not in control muscle biopsy tissues. To ensure comparability, FIGS. 8A-8C and 8D-8F were obtained using identical exposure settings for each channel. Results are representative of the staining seen in six anti-HMGCR-positive and three normal muscle biopsy samples. Original magnification ×20.

HMG-CoA Reductase Expression is Upregulated in Regenerating Muscle Fibers in Anti-HMG-CoA Reductase Autoantibody-Positive Patients To directly examine HMG-CoA reductase expression in vivo, muscle biopsy sections were stained with a commercially-available polyclonal anti-HMG-CoA reductase antibody (Millipore, Billerica, Mass.). Because other myositis-associated autoantigens are expressed at high levels in muscle cells with features of regeneration (Casciola-Rosen et al., *J Exp Med* 2005; 201:591-601 and Mammen et al, *Arthritis Rheum* 2009; 60: 3784-93), muscle biopsy sections were co-stained with an anti-NCAM antibody (Santa Cruz Biotechnology, Santa Cruz, Calif.). NCAM (Neural Cell Adhesion Molecule), an established marker of muscle regeneration. In muscle biopsy specimens showing normal features, HMGCR (FIG. 8E) and NCAM (FIG. 8D) were expressed at relatively low levels (see also FIG. 8F). In contrast, NCAM positive fibers were prominent in muscle biopsy samples obtained from anti-HMGCR-CoA reductase autoantibody-positive patients (who had not taken statins for months to years).), NCAM-positive fibers were prominent (FIG. 8A). Interestingly, most of these NCAM-positive fibers also expressed high levels of HMGCR-CoA reductase (FIGS. 8B-C). These findings provide in vivo confirmation that regenerating muscle fibers from anti-HMG 7R-positive patients express high levels of HMGCR.

Statins are a widely prescribed class of medications with known adverse effects on muscles, usually mild. Novel autoantibodies that recognize 200-kd and 100-kd proteins associated with autoimmune Myopathy and statin use were described herein above. The results reported herein demonstrate a plausible causal link between statin exposure and this distinct form of IMNM though identification of the autoantigen as HMGCR. Immunoprecipitation assays demonstrated the specificity of the autoantibodies for the carboxy-terminus of this enzyme, while competition experiments confirmed that anti-HMGCR autoantibodies immunoprecipitated both HMGCR and the 200-kd protein. The larger protein may be an associated protein or a multimer of HMGCR. The latter possibility is supported by other studies showing that HMGCR can be immunoprecipitated as a 97-kd monomer and as a 200-kd dimer (Parker et al., *J Biol Chem* 1989; 264:4877-87).

Having identified HMGCR as the relevant auto-antigen, an ELISA was developed to rapidly screen patient sera. Using this ELISA, the prevalence of anti-HMGCR autoantibodies was found to be 6% among patients with suspected myopathy who presented to the Johns Hopkins Myositis Center. Anti-HMGCR autoantibodies were preferentially identified in patients with a necrotizing myopathy on muscle biopsy and were not found in patients with IBM, DM, or normal controls. Thus, anti-HMGCR autoantibodies are one of the most frequent autoantibodies in the cohort, second only to anti-Jo-1. Since necrotizing myopathy is not always immune mediated, the detection of anti-HMGCR by ELISA is likely to be diagnostically helpful for the identification of patients with this form of IMNM, the majority of whom respond to immunosuppressive therapy.

Among the 45 anti-HMGCR-positive patients, one had Jo-1-positive antisynthetase syndrome (2.2%), and another had scleroderma with anti-PM-Scl auto-antibodies (2.2%). Therefore, as with other forms of autoimmune muscle disease, patients with anti-HMGCR autoantibodies may, in rare cases, have an overlap syndrome with another connective tissue disease.

Importantly, muscle expression of HMG-CoA reductase is increased with statin exposure, as well as in regenerating muscle cells marked by NCAM expression. This indicates that immune-mediated muscle damage initiated in the presence of statins and associated with anti-HMG-CoA reductase autoantibodies may be sustained even after the statin is discontinued, through persistently increased HMG-CoA reductase expression associated with muscle repair.

Since most patients taking statins do not develop an immune-mediated myopathy, other factors, including genetic susceptibility, must also play a role. The most common genetic factor predisposing patients to self-limited statin myopathy is the presence of the rs4149056 C allele, which accounts for up to 60% of statin myopathies in patients taking 80 mg of simvastatin daily (SEARCH Collaborative Group 2008). This polymorphism most likely increases the risk of myopathy by decreasing the hepatic uptake of statins by the OATP-1B1 transporter. However, this genetic alteration was not overrepresented in anti-HMG-CoA reductase autoantibody-positive patients, suggesting that other genetic susceptibilities or environmental coexposures are required for the development of the autoimmune response.

Interestingly, thirty-three percent of the anti-HMG-CoA reductase autoantibody-positive patients had not previously taken statins. Although these patients were younger at the time of disease onset and had higher creatine kinase levels, they also had an apparently immune-mediated myopathy and were otherwise indistinguishable from those with statin exposure. It is likely that other genetic and/or environmental factors may cause high levels of HMG-CoA reductase expression in these patients.

Because the clinic patients described herein presented with weakness and other prominent features of myopathy, this study does not address how prevalent anti-HMGCR autoantibodies are among patients taking statins who have milder symptoms. However, not one anti-HMGCR-positive patient was identified with persistent statin-induced myalgias who had no other compelling clinical evidence of myopathy. This indicates that an auto-immune response may also be associated with low-grade myopathic symptoms in some patients.

The results reported herein above in Examples 1-4 were obtained using the following materials and methods.

Patients.

Two hundred twenty-five patients with banked sera, muscle biopsy specimens available for review, and a myopathy as defined by proximal muscle weakness, elevated creatine kinase (CK) levels, myopathic electromyography (EMG) findings, muscle edema on magnetic resonance imaging (MRI), and/or features of myopathy on muscle biopsy were enrolled in a longitudinal study, approved by the Johns Hopkins Institutional Review Board, from March 2007 through December 2008. In addition to providing a history and undergoing physical examination at the Johns Hopkins Myositis Center, these patients underwent a comprehensive evaluation including some or all of the following: (1) electromyography and nerve conduction studies, (2) noncontrast bilateral thigh MRI, (3) pulmonary function tests, (4) malignancy screening including computed tomography scans of the chest, abdomen, and pelvis, (5) a standard laboratory evaluation performed by several different commercial laboratories including CK levels, antinuclear antibody (ANA) screen, erythrocyte sedimentation rate (ESR), C-reactive protein (CRP) levels, anti-Ro/La screen, and myositis-specific autoantibody (MSA) screen, and (6) when suspected based on clinical or biopsy features, testing for inherited muscle disease including limb-girdle muscular dystrophies (by Limb Girdle Muscular Dystrophy Evaluation panel: Athena Diagnostics, Worcester, Mass.), acid maltase deficiency (by Glycogen Storage Myopathy 'A' Profile: Athena Diagnostics and/or dried blood spot test for $\alpha$-glucosidase activity: Genzyme, Cambridge, Mass.), and/or facioscapulohumeral dystrophy (by Facioscalpulohumeral muscular dystrophy (FSHD) DNA Test: Athena Diagnostics).

In order to determine whether statins were used at an increased frequency in patients with the anti-200/100-kD autoantibody, the frequency of statin use was determined for patients in the cohort who had definite or probable polymyositis (PM) or dermatomyositis (DM) (Bohan and Peter, *N Engl J Med* 1975; 292:344-7 and 292:403-7) as well as in those with possible inclusion body myositis (IBM) (Griggs R C, et al., *Ann Neurol* 1995; 38:705-13). The ages of the patients were compared using Student's 2-tailed t-tests. The chi-square test was used to compare the frequency of statin use in the different groups.

Muscle Biopsy Analysis.

Muscle biopsy specimens were obtained from the deltoid, biceps, or quadriceps muscle groups. In each case, the muscle selected was determined to be weak by the examining physician. The slides from muscle biopsy specimens were evaluated at the Johns Hopkins Neu-romuscular Pathology Laboratory. These studies included hematoxylin and eosin-stained tissue as well as some or all of the following stains: modified Gomori's trichrome, adenosine triphosphatase at pH 4.3, pH 4.6, and pH 9.4, NAD tetrazolium reductase, acid phosphatase, succinic dehydrogenase, cytochrome oxidase, esterase, alkaline phosphatase, periodic acid-Schiff (PAS), PAS-diastase control, and Congo red. Both frozen and paraffin-embedded specimens were routinely screened for the presence of degenerating, regenerating, and/or necrotic fibers, primary endomysial inflammation, perivascular inflammation, rimmed vacuoles, perifascicular atrophy, and fibrosis. We identified "necrotizing myopathy" biopsy specimens based on the presence of necrotic muscle fibers as the predominant abnormal histologic feature; with the exception of necrotic myofibers undergoing myophagocytosis, inflammatory cells were sparse, if present at all. Muscle biopsy specimens from patients with the anti-200/100-kD autoantibody specificity were stained with antibodies recognizing CD31 (an endothelial cell marker), C5b-9 (i.e., membrane attack complex), and class I major histocompatibility complex (MHC).

Briefly, 7-μ thick frozen muscle biopsy sections were fixed in ice-cold acetone. After ten minutes in peroxidase blocking reagent (Dako, Carpinteria, Calif.) at room temperature, sections were incubated with 5% bovine serum albumin/phosphate buffered saline (BSA/PBS) for one hour at 37° C. Primary antibodies were prepared in 1% BSA/PBS at the following dilutions: 1:50 for class I MHC (Santa Cruz Biotechnology, Santa Cruz, Calif.), 1:20 for CD31 (Dako), 1:50 for Cb5-9 (Santa Cruz Biotechnology); primary incubations were performed overnight at 4° C. After PBS washes, the slides were incubated with horseradish peroxidase-labeled goat anti-mouse secondary antibody (Dako) in 1% BSA/PBS at 1:500 for one hour at room temperature. The compound 3,3'-diaminobenzidine chromagen (Dako) was used to visualize each antibody, and all sections were counterstained with hematoxylin. Normal muscle tissue samples were used as negative controls, and muscle tissue from a Jo-1-positive patient with myositis was used as a positive control for class I MHC staining. For each primary antibody, all muscle sections were processed simultaneously under the same conditions.

Immunoprecipitations.

Serum samples collected from each patient were stored at −80° C. HeLa cells cultured using standard procedures were radiolabeled for two hours with 100 μCi/ml $^{35}$S-methionine and cysteine (MP Biomedicals, Solon, Ohio) in methionine-free and cysteine-free medium. The cells were subsequently lysed in buffer A (50 mM Tris pH 7.4, 150 mM NaCl, 5 mM EDTA, 0.5% Nonidet P40, 0.5% sodium deoxycholate, 0.1% sodium dodecyl sulfate (SDS), and a protease inhibitor cocktail). Each 10-cm dish was lysed in 1 ml buffer A and was used for 10 immunoprecipitations. Immunoprecipitations were performed by adding 1 μl of patient sera to 100 μl radiolabeled lysate and bringing the volume to 1 ml with buffer B (1% Nonidet P40, 20 mM Tris pH 7.4, 150 mM NaCl, 1 mM EDTA, and a protease inhibitor cocktail) and rotating the mix for one hour at 4° C. Protein A agarose beads (Pierce, Rockford, Ill.) were used to precipitate the antibody-antigen complexes that were subsequently electrophoresed on 10% SDS-polyacrylamide gels. The radiolabeled immunoprecipitates were visualized by fluorography.

The results reported herein in Examples 5-11 above were obtained using the following materials and methods.

Patients and Genotyping.

Between May 2002 and April 2010, 750 patients in whom myopathy was suspected, as defined by proximal muscle weakness, elevated creatine kinase (CK) levels, myopathic findings on electromyography (EMG), muscle edema on magnetic resonance imaging (MRI), and/or myopathic features on muscle biopsy, were enrolled in a longitudinal study. Patients were defined as having polymyositis (PM) or dermatomyositis (DM) if they had probable or definite disease according to the Bohan and Peter criteria (Bohan and Peter, *N Engl J Med* 1975; 292:344-7 and 403-7) and as having inclusion body myositis (IBM) if they met the Griggs et al. criteria for possible disease (Griggs et al., *Ann Neurol* 1995; 38:705-13). Serum was available from each subject and DNA samples were available from 260 subjects. Serum samples from twenty healthy control subjects without prior statin exposure were also obtained. All subjects were enrolled in protocols approved by the Johns Hopkins Institutional Review Board. Genotyping of the rs4149056 C allele was performed using the appropriate verified TaqMan® Drug Metabolism Genotyping Assay (Applied Biosystems, Carlsbad, Calif.) on all seventeen anti-HMG-CoA reductase-positive patients for whom DNA samples were available (see Table 4 for detailed clinical information).

Immunoprecipitations from Radiolabeled Cell Lysates.

HeLa cells were cultured in the absence or presence of 10 μM mevinolin (Sigma, St. Louis, Mo.) for 22 hours and were then radiolabeled with 100 μCi/ml of $^{35}$S-methionine/cysteine (MP Biomedicals, Solon, Ohio), lysed, and immunoprecipitated with patient sera (See Examples 1-4, above). Immunoprecipitates were reduced, boiled, subjected to electrophoresis 10% sodium dodecyl sulfate-polyacrylamide gels, and visualized by fluorography.

Immunoprecipitations Using $^{35}$S-Methionine-Labeled In Vitro Transcription/Translated (IVTT) Proteins.

DNA encoding full-length human HMG-CoA reductase was purchased from Invitrogen (Carlsbad, Calif.). DNA encoding the N-terminal fragment (amino acids (aa) 1-377) was generated by mutating R377 to a stop codon. DNA encoding the C-terminus of HMG-CoA reductase (aa 340-888) was prepared by polymerase chain reaction (PCR) using the full-length DNA as a template. Constructs were sequence verified and used in IVTT reactions (Promega, Madison, Wis.), generating $^{35}$S-methionine-labeled proteins. Immunoprecipitations using these products were performed, with detection of the immunoprecipitates as described above.

Competition Experiments.

One microliter of each patient serum was preincubated (30 minutes at 4° C. in 50 μl) with the catalytic domain of human HMG-CoA reductase (aa 426-888) expressed as a fusion protein with glutathione S-transferase (hereinafter referred to as "C-terminal HMG-CoA reductase"; Sigma). Preincubated antibodies were subsequently used for immunoprecipitations with full-length IVTT HMG-CoA reductase or radiolabeled lysates made from mevinolin-treated HeLa cells.

Anti-HMGCR ELISA.

ELISA plates (96-well) were coated overnight at 4° C. with 100 ng of C-terminal HMG-CoA reductase (Sigma) diluted in phosphate buffered saline (PBS). Replicate wells were incubated with PBS alone. After washing the plates, human serum samples diluted 1:400 in PBS with 0.05% Tween-20 were added to the wells for one hour at 37° C. After washing, horseradish peroxidase-labeled goat anti-human antibody (1:10,000; Pierce, Rockford, Ill.) was added to each well for 30 minutes at 37° C. Color development was performed using SureBlue™ peroxidase reagent (KPL, Gaithersburg, Md.) and the absorbance at 450 nm was determined. For each sample, the background absorbance from the PBS-coated wells was subtracted from that of the corresponding C-terminal HMG-CoA reductase-coated well. Test sample absorbance was expressed as a proportion of the absorbance in an arbitrary positive control sample (sample 9176), a reference serum included in every ELISA.

Immunohistochemistry.

The collection and use of human biopsy specimens was approved by the Johns Hopkins Institutional Review Board. Muscle biopsy specimens from 6 patients with anti-HMGCR antibody and 3 normal control subjects were studied. All biopsy specimens were obtained from patients who had not taken statins for greater than three months. Staining of paraffin sections was performed as described previously (9). Antibody incubations comprised mixtures of rabbit anti-HMGCR (Millipore) and mouse anti-neural cell adhesion molecule (anti-NCAM; Santa Cruz Biotechnology) primary antibodies, followed by donkey anti-rabbit IgG Alexa Fluor 594 (to detect HMGCR) and donkey anti-mouse IgG. Alexa Fluor 488 (to detect NCAM) secondary antibodies (Invitrogen).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for characterizing a myopathy in a subject, the method comprising detecting in a biological sample of the subject increased levels of an autoantibody that recognizes a 3-hydroxy-3-methylglutaryl coenzyme A reductase (HMGCR) protein relative to a reference level.

2. The method of claim 1 further comprising detecting in the biological sample of the subject a 100 kD protein and/or a 200 kD protein that binds an HMGCR antibody.

3. The method of claim 1, wherein the myopathy is an autoimmune-mediated myopathy or necrotizing myopathy associated with statin therapy.

4. The method of claim 1, wherein the method further comprises characterizing proximal muscle strength, muscle edema on bilateral thigh magnetic resonance imaging (MRI), creatine kinase levels, and/or myopathic findings on electromyography.

5. The method of claim 1, further comprising detecting a marker selected from the group consisting of antisynthetase autoantibodies, anti-signal recognition particle (SRP) autoantibodies, elevated creatine kinase (CK) levels, marked inflammatory cell infiltrates in muscle biopsy, rimmed vacuoles, perifascicular atrophy, class I MHC positive, membrane attack complex deposition in small perimysial blood vessels, and anti-NCAM antibody staining of regenerating muscle fibers.

6. The method of claim 1, wherein the biological sample is a liquid biological sample or a tissue sample.

7. The method of claim 1, wherein the autoantibody is detected in an immunoassay.

8. The method of claim 7, wherein the immunoassay is selected from the group consisting of an enzyme linked immunosorbent assay (ELISA), an immunoprecipitation assay, a fluorescent immunosorbent assay, a chemical linked immunosorbent assay, a radioimmunoassay, an immunoblotting assay, and immunometric assay, a flow cytometry assay, a Western blot, and an immunohistochemistry assay.

9. The method of claim 1, wherein the HMGCR protein is fixed to a substrate.

10. The method of claim 9, where the substrate is a membrane, a bead, or a microchip.

11. The method of claim 1, wherein the reference level is a normal control.

12. The method of claim 1, wherein the HMGCR proteins is the full length protein or a fragment thereof having HMGCR antibody binding activity.

13. The method of claim 12, wherein the HMGCR protein fragment comprises amino acids 340-888 of the HMGCR protein.

14. The method of claim 1, further comprising detecting myositis-specific autoantibodies (MSAs).

15. A method for characterizing a myopathy in a subject, the method comprising detecting in a biological sample of the subject increased levels of a 100 kD protein and/or a 200 kD protein that binds an HMGCR antibody relative to a reference level.

16. The method of claim 15, wherein the myopathy is an autoimmune-mediated myopathy or necrotizing myopathy associated with statin therapy.

17. The method of claim 15, wherein the method further comprises characterizing proximal muscle strength, muscle edema on bilateral thigh magnetic resonance imaging (MRI), creatine kinase levels, and/or myopathic findings on electromyography.

18. The method of claim 15, further comprising detecting a marker selected from the group consisting of antisynthetase autoantibodies, anti-signal recognition particle (SRP) autoantibodies, elevated creatine kinase (CK) levels, marked inflammatory cell infiltrates in muscle biopsy, rimmed vacuoles, perifascicular atrophy, class I MHC positive, membrane attack complex deposition in small perimysial blood vessels, and anti-NCAM antibody staining of regenerating muscle fibers.

19. The method of claim 15, wherein the autoantibody is detected in an immunoassay selected from the group consisting of an enzyme linked immunosorbent assay (ELISA), an immunoprecipitation assay, a fluorescent immunosorbent assay, a chemical linked immunosorbent assay, a radioimmunoassay, an immunoblotting assay, and immunometric assay, a flow cytometry assay, a Western blot, and an immunohistochemistry assay.

20. A method for characterizing a myopathy in a subject, the method comprising detecting in a biological sample of the subject increased levels of an autoantibody that recognizes amino acids 340-888 of a 3-hydroxy-3-methylglutaryl coenzyme A reductase (HMGCR) protein relative to a reference level, wherein the autoantibody is detected in an immunoassay.

* * * * *